(12) United States Patent
Amin et al.

(10) Patent No.: US 10,568,873 B1
(45) Date of Patent: Feb. 25, 2020

(54) SAFRANAL-SORAFENIB COMBINATION THERAPY FOR LIVER CANCER

(71) Applicant: United Arab Emirates University, Al Ain (AE)

(72) Inventors: Amr Amin, Al Ain (AE); Ameera AlMansoori, Al Ain (AE); Badriya Baig, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 16/275,878

(22) Filed: Feb. 14, 2019

(51) Int. Cl.
  *A61K 31/44* (2006.01)
  *A61K 31/122* (2006.01)
  *A61P 35/00* (2006.01)
  *A61K 36/88* (2006.01)
  *A61K 9/00* (2006.01)

(52) U.S. Cl.
  CPC .......... *A61K 31/44* (2013.01); *A61K 9/0053* (2013.01); *A61K 31/122* (2013.01); *A61K 36/88* (2013.01); *A61P 35/00* (2018.01)

(58) Field of Classification Search
  CPC ...... A61K 31/11; A61K 31/44; A61K 31/122; A61K 9/0053; A61K 36/88; A61P 35/00
  See application file for complete search history.

(56) References Cited

U.S. PATENT DOCUMENTS

| | | | | |
|---|---|---|---|---|
| 2009/0215835 | A1* | 8/2009 | Wilhelm | A61K 31/44 514/350 |
| 2010/0120816 | A1* | 5/2010 | Fontana | C07D 491/22 514/283 |

OTHER PUBLICATIONS

Remington: The Science and Practice of Pharmacy, 2005, 21st ed., pp. 1023, 1034-1036, 1823-1839 (Year: 2005).*
Lv et al., "Agrin para-secreted by PDGF-activated human hepatic stellate cells promotes hepatocarcinogenesis in vitro and in vivo", Oncotarget, 2017, vol. 8, No. 62, pp. 105340-105355, 16 pages.
Machado et al., "Histopathological lesions, P-glycoprotein and PCNA expression in zebrafish (*Danio rerio*) liver after a single exposure to diethylnitrosamine", Elsevier, Science Direct, Environmental Toxicology and Pharmacology, 2014, vol. 38, No. 3, pp. 720-732, 13 pages.
Moreira et al., "Melatonin Activates Endoplasmic Reticulum Stress and Apoptosis in Rats with Diethylnitrosamine-Induced Hepatocarcinogenesis", Research Article, PLoS ONE, 2015, vol. 10, No. 12.
Mouri et al., "Combination therapy with carboplatin and paclitaxel for small cell lung cancer", Elsevier, Respiratory Investigation, 2019, vol. 57, No. 1, pp. 34-39, 6 pages.
Nair & Jacob, "A simple practical guide for dose conversion between animal and human", Journal of Basic and Clinical Pharmacy, Wolters Kluwer-Medknow, 2016, vol. 7, No. 2, pp. 27-31, 6 pages.
Nair & Staden, "Cell cycle modulatory effects of Amaryllidaceae alkaloids", Elsevier, Life Sciences, 2018, vol. 213, pp. 94-101, 8 pages.
Ozkececi et al., "Investigation of the effect of safranal and crocin pre-treatment on hepatic injury induced by infrarenal aortic occlusion". Elsevier, Science Direct, Biomedicine & Pharmacotherapy, 2016, vol. 83, pp. 160-166, 7 pages.
Pang & Lam, "Surgical management of hepatocellular carcinoma", World Journal of Hepatology, 2015, vol. 7, No. 2, pp. 245-252, 9 pages.
Prinsloo et al., "The use of plants containing genotoxic carcinogens as foods and medicine", Elsevier, Science Direct, Food and Chemical Toxicology, 2018, vol. 116, pp. 27-39. 13 pages.
Ramakrishna et al., "From Cirrhosis to Hepatocellular Carcinoma: New Molecular Insights on Inflammation and Cellular Senescence", Liver Cancer, Karger AG, Basel, 2013, vol. 2, pp. 367-383, 17 pages.
Rana & Rana, "Review on Present Status and Future of Herbal Medicine", The Beats of Natural Sciences, 2014, vol. 1, No. 2, 8 pages.
Rates, "Plants as source of drugs", Elsevier, Toxicon, 2001, vol. 39, pp. 603-613, 11 pages.
Rezaee & Hosseinzadeh, "Safranal: From an Aromatic Natural Product to a Rewarding Pharmacological Agent", Iranian Journal of Basic Medical Sciences, 2013, vol. 16, No. 1, pp. 12-26, 15 pages.
Samarghandian et al., "Anti-tumor activity of safranal against neuroblastoma cells", Pharmacognosy Magazine, 2014, vol. 10(Suppl 2), pp. S419-S424, 7 pages.
Santos et al., "Animal models as a tool in hepatocellular carcinoma research: A Review", Tumor Biology, SAGE, 2017, vol. 39, No. 3, 20 pages.
Singhi et al., "Reticulin loss in benign fatty liver: an important diagnostic pitfall when considering a diagnosis of hepatocellular carcinoma", The American Journal of Surgical Pathology, 2012, vol. 36, No. 5, pp. 710-715, 6 pages.
Baig et al., "Cancer and Biotechnology: A Matchup that Should Never Slowdown", Chapter 3, Biotechnology and Production of Anti-Cancer Compounds, Springer International Publishing, 2017, pp. 73-97, 26 pages.
Srivastava et al., "*Crocus sativus* L.: A comprehensive review", Pharmacognosy Reviews, Publication of Pharmacognosy Network Worldwide, Medknow Publications, 2010, vol. 4, No. 8, pp. 200-208, 11 pages.
Subramaniam, et al., "Potential role of signal transducer and activator of transcription (STAT)3 signaling pathway inflammation, survival, proliferation and invasion of hepatocellular carcinoma", Elsevier, Biochimica et Biophysica Acta (BBA)—Reviews on Cancer, 2013, vol. 1835, No. 1, pp. 46-60, 15 pages.

(Continued)

*Primary Examiner* — Sarah Pihonak
(74) *Attorney, Agent, or Firm* — Hayes Soloway P.C.

(57) ABSTRACT

A therapeutic combination of drugs for the treatment of a liver cancer includes safranal or a pharmaceutically acceptable pro-drug thereof, and sorafenib. In representative embodiments, the pro-drug is selected from the group of a safranal salt, hydrate, hemiacetal, acetal, thioacetal, silylether, tautomer, isomer, and combinations thereof. The safranal and the sorafenib may be compounded together in a same unitary pharmaceutical composition including both compounds. Alternatively, the safranal and the sorafenib may be provided in the form of separate pharmaceutical compositions.

20 Claims, 14 Drawing Sheets

(56) References Cited

OTHER PUBLICATIONS

Tadmouri & Al-Sharhan, "Cancers in the United Arab Emirates", Genetic Disorders in the Arab World: United Arab Emirates, 2004, pp. 59-61, 3 pages.
Wang et al., "Proliferating cell nuclear antigen promotes cell proliferation and tumorigenesis by up-regulating STAT3 in non-small cell lung cancer", Elsevier, Biomedicine & Pharmacotherapy, 2018, vol. 104, pp. 595-602, 8 pages.
Wen et al., "Collapsed Reticular Network and its Possible Mechanism during the Initiation and/or Progression of Hepatic Fibrosis", Scientific Reports, vol. 6, No. 35426,11 pages.
Xie et al., "miR-152 inhibits proliferation of human endometrial cancer cells via inducing G2/M phase arrest by suppressing CDC25B expression", Elsevier, Biomedicine & Pharmacotherapy, 2018, vol. 99, pp. 299-305, 7 pages.
Yao et al., "Diagnostic Value of Immunohistochemical Staining of GP73, GPC3, DCP, CD34, CD31, and Reticulin Staining in Hepatocellular Carcinoma", Journal of Histochemistry and Cytochemistry, 2013, vol. 61, No. 9, pp. 639-648, 10 pages.
Yinti et al., "Analysis of reticulin fiber pattern in lymph nodes with metastasis from oral squamous cell carcinoma", Dental Hypotheses, Wolters Kluwer-Medknow, 2015, vol. 6, No. 3, pp. 104-108, 5 pages.
Zhang et al., "The activation of p38 and JNK by ROS, contribute to OLO-2-mediated intrinsic apoptosis in human hepatocellular carcinoma cells", Elsevier, Food and Chemical Toxicology, 2014, vol. 63, pp. 38-47, 10 pages.
Zhou et al., "Systematic Review with Network Meta-Analysis: Antidiabetic Medication and Risk of Hepatocellular Carcinoma". Scientific Reports, 2016, vol. 6, 10 pages.
Amin et al., "Evasion of anti-growth signaling: A key step in tumorigenesis and potential target for treatment and prophylaxis by natural compounds". Elsevier, Seminars in Cancer Biology, 2015, vol. 35, pp. S55-S77, 23 pages.
Yaswen et al., "Therapeutic targeting of replicative immortality" Elsevier, Seminars in Cancer Biology, 2015, vol. 35, pp. S104-S128, 25 pages.
Samadi et al., "A multi-targeted approach to suppress tumor-promoting inflammation". Elsevier, Seminars in Cancer Biology, 2015, vol. 35, pp. S151-S184, 34 pages.
Amin & Lowe, "Plant-Based Anticancer Drug Development: Advancements and Hurdles", Journal of Gastrointestinal & Digestive System, 2012, vol. 2, No. 5, 2 pages.
Block et al., "Designing a broad-spectrum integrative approach for cancer prevention and treatment", Elsevier, Seminars in Cancer Biology, 2015, vol. 35, pp. S276-S304, 29 pages.
Al-Hrout et al., "Cancer and Biotechnology: A Matchup that Should Never Slowdown", Chapter 3, Biotechnology and Production of Anti-Cancer Compounds, Springer International Publishing, 2017, pp. 73-97, 26 pages.
Amin et al., "Defective Autophagosome Formation in p53-Null Colorectal Cancer Reinforces Crocin-Induced Apoptosis", International Journal of Molecular Sciences, 2015, vol. 16, pp. 1544-1561, 18 pages.
Hamza et al., "Melissa officinalis Protects against Doxorubicin-Induced Cardiotoxicity in Rats and Potentiates Its Anticancer Activity on MCF-7 Cells", PLOSone, 2016, 25 pages.
Ai-Akhras et al, "Introducing Cichorium Pumilum as a Potential Therapeutical Agent Against Drug-Induced Benign Breast Tumor in Rats", Informa Healthcare USA, Inc., Electromagnetic Biology and Medicine, 2012, 12 pages.
Amin et al., "Neural network assessment of herbal protection against chemotherapeutic-induced reproductive toxicity", BioMed Central, Theoretical Biology and Medical Modelling, 2012, vol. 9, No. 1, 15 pages.
Amin, "Protective Effect of Green Algae Against 7,12-Dimethylbenzanthracene (DMBA)-Induced Breast Cancer Rats", International Journal of Cancer Research, 2009, vol. 5, No. 1, pp. 12-24, 14 pages.
Ai-Akhras et al., "In Vitro Studies on the Effect of Phototoxicity of a New Photosensitizer Extracted from Flowers and Aerial Parts of Cichorium pumilum", American Journal of Pharmacology and Toxicology, 2007, vol. 2, No. 2, pp. 39-45, 8 pages.
Liu et al., "Molecular Serum Markers of Liver Fibrosis", Biomarker Insights, Libertas Academica Freedom to Research, 2012, vol. 7, pp. 105-117, 13 pages.
Ferlay, J. et al., "Cancer incidence and mortality worldwide: Sources, methods and major patterns in GLOBOCAN 2012", International Journal of Cancer, 2015, vol. 136, Issue 5, 2014, pp. E359-E386, 28 pages.
Sherman, "Hepatocellular Carcinoma: Epidemiology, Surveillance, and Diagnosis", Seminar in Liver Disease, Department of Medicine, University of Toronto and University Health Network, Toronto, Canada, Thieme Medical Publishers, Inc., 2010, vol. 30, No. 1, 14 pages.
Nahon, et al., "Hepatic iron overload and risk of hepatocellular carcinoma in cirrhosis", Elsevier Masson, ScienceDirect, US National Library of Medicine, Gastroenterologie Clinique et. Biologique, 2009, vol. 34, Issue 1, pages 1-7, 7 pages.
Starley et al., "Nonalcoholic fatty liver disease and hepatocellular carcinoma: a weighty connection", Hepatology, vol. 51, No. 5, 2010, pp. 1820-1832, 13 pages.
Kinghorn et al., "Discovery of Natural Product Anticancer Agents from Biodiverse Organisms", Curr. Opin. Drug Discov. Devel., 2009, vol. 12, pp. 189-196, 12 pages.
Newman, D. J. & Cragg, G. M., "Natural products as sources of new drugs from 1981 to 2014", Journal of Natural Products, 2016, vol. 79, pp. 629-661, 33 pages.
Greenlee, "Natural products for cancer prevention" Semin. Oncol. Nurs., 2012, vol. 28, pp. 29-44, 16 pages.
Bachrach, "Contribution of selected medicinal plants for cancer prevention and therapy", Acta Facultatis Medicae Naissensis, 2012, vol. 29, No. 3, 7 pages.
Amin et al., "Saffron-based crocin prevents early lesions of liver cancer: In vivo, In vitro and network Analyses", Recent Pat Anticancer Drug Discovery, 2016, vol. 11, pp. 121-133, 13 pages.
Amin et al., "Saffron: A potential candidate for a novel anticancer drug against hepatocellular carcinoma", Hepatology, 2011, vol. 54, pp. 857-867, 11 pages.
Samarghandian, et al., "Anti-tumor activity of safranal against neuroblastoma cells", Pharmacognosy Magazine, 2014, vol. 10, pp. S419-S424, 11 pages.
Samarghandian & Shabestari, "DNA fragmentation and apoptosis induced by safranal in human prostate cancer cell line", Indian Journal of Urology, 2013, vol. 29, pp. 177-183, 13 pages.
Escribano, et al., "Crocin, safranal and picrocrocin from saffron (Crocus sativus L.) inhibit the growth of human cancer cells in vitro", Cancer Letters, Elsevier, 1996, vol. 100, pp. 23-30, 8 pages.
Assimopoulou et al., "Radical Scavenging Activity of Crocus sativus L. Extract and its Bioactive Constituents", Phytotherapy Research, 2005, Voume 19, pp. 997-1000, 4 pages.
Samarghandian & Boskabady, "Caspase-dependent pathway in apoptosis induced by Safranal in alveolar human lung cancer cell line", Research in Pharmaceutical Sciences, 2012, vol. 7, 1 page.
Sharma et al., "Histone H2AX phosphorylation: a marker for DNA damage", 2012, Methods in Molecular Biology, vol. 920, 613-626, 15 pages.
Warmerdam & Kanaar, "Dealing with DNA damage: Relationships between checkpoint and repair pathways", Mutation Research—Reviews in Mutation Research, 2010, vol. 704, pp. 2-11, 10 pages.
Zhang et al., "Safranal inhibits the migration and invasion of human oral squamous cell carcinoma cells by overcoming epithelial-mesenchymal transition", Biomedical Research, 2017, vol. 28, pp. 817-821, 5 pages.
Samarghandian & Borji, "Anticarcinogenic effect of saffron (Crocus sativus L) and its ingredients", Pharmacognosy Research, 2014, vol. 6, pp. 99-107, 15 pages.
Milajerdi et al., "The toxicity of saffron (Crocus sativus L) and its constituents against normal and cancer cells", Journal of Nutrion & Intermediary Metabolism, 2016, vol. 3, pp. 23-32, 39 pages.

(56) References Cited

OTHER PUBLICATIONS

Nigam et al., "Targeting mortalin by embelin causes activation of tumor suppressor p53 and deactivation of metastatic signaling in human breast cancer cells", PLoS One, 2015, vol. 10, 16 pages.
Hu et al., :Lycorine is a novel inhibitor of the growth and metastasis of hormone-refractory prostate cancer, Oncotarget, Advance Publications, 2015, vol. 6, 15 pages.
Wang et al., "Baicalein induces apoptosis and autophagy via endoplasmic reticulum stress in hepatocellular carcinoma cells", Biomed Research International, 2014, vol. 2014, 14 pages.
Contour-Galcera et al., "What's new on CDC25 phosphatase inhibitors", Pharmacology and Therapeutics, 2007, vol. 115, 12 pages.
Lund et al., "Inhibition of CDC25B phosphatase through disruption of protein-protein interaction". ACS Chemical Biology, 2015, vol. 10, pp. 390-394, 5 pages.
Lavecchia et al., "CDC25 phosphatase inhibitors: an update", Mini-Reviewes in Medicinal Chemistry, 2102, vol. 12, pp. 62-73, 13 pages.
Lavecchia et al., "Cdc25B phosphatase inhibitors in cancer therapy: latest developments, trends and medicinal chemistry perspective", Anti-cancer Agents Medicinal Chemistry, 2008, vol. 8, pp. 843-856, 15 pages.
Ham et al., "Studies on menadione as an inhibitor of the cdc25 phosphatase", Bioorganic Chemistry, 1997, vol. 25, pp. 33-36, 4 pages.
Tamura et al., "Cdc25 inhibition and cell cycle arrest by a synthetic thioalkyl vitamin K analogue", Cancer Research, 2000, vol. 60, pp. 317-1325, 10 pages.
Wu et al., "UCN-01 induces S and G2/M cell cycle arrest through thep53/p21(waf1) or CHK2/CDC25C pathways and can suppress invasion in human hepatoma cell lines", 2013, vol. 13, No. 167, 10 pages.
Fragkos et al., "H2AX Is required for cell cycle arrest via the p53/p21 pathway", Molecullar and Cellular Biology, 2009, vol. 29, No. 10, pp. 2828-2840, 13 pages.
Das et al., "PARP1-TDP1 coupling for the repair of topoisomerase I-induced Dna damage", Nucleic Acids Research, 2014, vol. 42, No. 7, pp. 4435-4449, 15 pages.
Dexheimer et al., "Tyrosyl-DNA phosphodiesterase as a target for anticancer therapy", Anticancer Agents Med Chem., 2008, vol. 8, No. 4, pp. 381-389, 17 pages.
Pommier et al., "DNA topoisomerases and their poisoning by anticancer and antibacterial drugs", Chemistry and Biology Review, 2010, vol. 17, pp. 421-433, 13 pages.
Huang et al., "Tyrosyl-DNA Phosphodiesterase 1 (Tdp1) inhibitors", Expert Opin. Ther. Pat., 2011, vol. 21, No. 9, pp. 1285-1292, 10 pages.
Miller et al., "Human HDAC1 and HDAC2 function in the DNA-damage response to promote DNA nonhomologous endjoining". Nat. Struct. Mol. Biol., 2010, vol. 17, No. 9, pp. 1144-1151, 20 pages.
Roos & Kaina, "DNA damage-induced cell death by apoptosis", Elsevier, Trends in Molecular Medicine, 2006, vol. 12, No. 9, pp. 440-450, 11 pages.
McIlwain et al., "Caspase functions in cell death and disease", . Cold Spring Harbor Perspective in Biology, 2013, vol. 5, 28 pages.
Hamsa & Kuttan, "Harmine activates intrinsic and extrinsic pathways of apoptosis in B16F-10 melanoma". Chinese Medicine, 2011, vol. 6, No. 11, 8 pages.
Kang et al., "Inhibition of EGFR signaling augments oridonin-induced apoptosis in human laryngeal cancer cells via enhancing oxidative stress coincident with activation of both the intrinsic and extrinsic apoptotic pathways", Cancer Letters, Elsevier, 2010, vol. 294, pp. 147-158, 12 pages.
Hsieh et al., "Antcin B and its ester derivative from Antrodia camphorata induce apoptosis in hepatocellular carcinoma cells involves enhancing oxidative stress coincident with activation of intrinsic and extrinsic apoptotic pathway", Journal of Agricultural and Food Chemistry, 2011, vol. 59, pp. 10943-10954, 12 pages.

Momoi, "Caspases involved in ER stress-mediated cell death", Journal of Chemical Neuroanatomy, 2004, vol. 28, pp. 101-105, 5 pages.
Winter et al., "Involvement of extrinsic and intrinsic apoptotic pathways together with endoplasmic reticulum stress in cell death induced by naphthylchalcones in a leukemic cell line: Advantages of multi-target action", Elsevier, Toxicology in Vitro, 2014, vol. 28, pp. 769-777, 9 pages.
Pickart & Eddins, "Ubiquitin: structures, functions, mechanisms", Elsevier, Biochimica et Biophysica Acta—Molecular Cell Research, 2004, vol. 1695, pp. 55-72, 18 pages.
Tabas & Ron, "Integrating the mechanisms of apoptosis induced by endoplasmic reticulum stress", . Nat. Cell Biol., 2011, vol. 13, No. 3, pp. 184-190, 17 pages.
Pagliarini et al., "Downregulation of E2F1 during ER stress is required to induce apoptosis", Journal of Cell Science, 2015, vol. 128, pp. 1166-1179, 14 pages.
Lee, "GRP78 induction in cancer: therapeutic and prognostic implications", American Association for Cancer Research, 2007, pp. 3496-3499, 5 pages.
Rahmani et al., "The kinase inhibitor sorafenib induces cell death through a process involving induction of endoplasmic reticulum stress", Molecullar and Cellular Biology, 2007, vol. 27, No. 15, pp. 5499-513, 15 pages.
Han et al., "Endoplasmic reticulum stress inhibits cell cycle progression via induction of p27 in melanoma cells". Elsevier, Cellular Signalling, 2013, vol. 25, pp. 144-149. 6 pages.
Brewer et al., "Mammalian unfolded protein response inhibits cyclin D1 translation and cell-cycle progression", Proc. Natl. Acad. Sci. USA, 1999, vol. 96, pp. 8505-8510, 6 pages.
Mlynarczyk & Fåhraeus, "Endoplasmic reticulum stress sensitizes cells to DNA damage-induced apoptosis through p53-dependent suppression of p21 CDKN1A", Nature Communications, 2014, 16 pages.
Mihailidou et al., "CHOP-dependent regulation of p21/waf1 during ER stress", Cellular Physiology and Biochemistry, 2010, vol. 25, pp. 761-766, 6 pages.
Maytin et al., "Stress-inducible transcription factor CHOP/gadd153 induces apoptosis in mammalian cells via p38 kinase-dependent and -independent mechanisms", Experimental Cell Research, 2001, vol. 267, pp. 193-204, 12 pages.
Hamanaka et al., "PERK and GCN2 contribute to elF2alpha phosphorylation and cell cycle arrest after activation of the unfolded protein response pathway", Molecular Biology of the Cell, 2005, vol. 16, pp. 5493-5501, 9 pages.
Ng et al., "Curcumin sensitizes acute promyelocytic leukemia cells to unfolded protein response-induced apoptosis by blocking the loss of misfolded N-CoR protein" Molecular Cancer Research, 2011, vol. 9, pp. 878-888, 12 pages.
Huang et al., "Anacardic acid induces cell apoptosis associated with induction of ATF4-dependent endoplasmic reticulum stress", Elsevier, Toxicology Letters, 2014, vol. 228, pp. 170-178, 9 pages.
Teske et al., "The elF2 kinase PERK and the integrated stress response facilitate activation of ATF6 during endoplasmic reticulum stress", MBoC|Article, Molecular Biology of the Cell, 2011, 22, 4390-4405, 16 pages.
Estomes et al., "RIPK1 promotes death receptor-independent caspase-8-mediated apoptosis under unresolved ER stress conditions", Cell Death and Disease, 2014, vol. 5, e1555, 11 pages.
Jimbo et al., "ER stress induces caspase-8 activation, stimulating cytochrome c release and caspase-9 activation", Experimental Cell Research, Science Direct, 2003, vol. 283, pp. 156-166, 11 pages.
Iurlaro & Muñoz-Pinedo, "C. Cell death induced by endoplasmic reticulum stress", FEBS Journal 283, 2015, pp. 2640-2640, 13 pages.
Hiss & Gabriels, "Implications of endoplasmic reticulum stress, the unfolded protein response and apoptosis for molecular cancer therapy. Part I: targetingp53, Mdm2, GADD153/CHOP, GRP78/BiP and heat shock proteins", Expert Opinion Drug Discovery, 2009, vol. 4, pp. 799-821, 23 pages.
Nalepa et al., "Drug discovery in the ubiquitin-proteasome system", . Nature Reviews Drug Discovery, 2006, vol. 5, pp. 596-613, 19 pages.

(56) References Cited

OTHER PUBLICATIONS

Zavrski et al., "Molecular and clinical aspects of proteasome inhibition in the treatment of cancer", Recent Results Cancer Research, 2007, vol. 176, pp. 165-176, 13 pages.
Saleh et al., "Antagonism between curcumin and the topoisomerase II inhibitor etoposide: A study of DNA damage, cell cycle regulation and death pathways", Cancer Biology & Therapy, 2012, vol. 13, pp. 1058-1071, 14 pages.
Krämer et al., "Causal analysis approaches in Ingenuity Pathway Analysis", Bioinformatics, vol. 30, No. 4, pp. 523-530, 8 pages.
Ahmad et al., "Role of traditional Islamic and Arabic plants in cancer therapy", Journal of Traditional and Complementary Medicine, 2017, vol. 7, pp. 195-204, 10 pages.
Aldridge et al., "The use of total protein stains as loading controls: an alternative to high-abundance single protein controls in semi-quantitative immunoblotting", Journal of Neuroscience Methods, 2008, vol. 172, No. 2, pp. 250-254, 10 pages.
Al-Hrout et al., "Safranal induces DNA double-strand breakage and ERstress-mediated cell death in hepatocellular carcinoma cells", Scientific Reports, 2018, vol. 8, 15 pages.
Alsaied et al., "Sorafenib and triptolide as combination therapy for hepatocellular carcinoma", Surgery, 2014, vol. 156, No. 2, pp. 270-279, 10 pages.
Amin et al., "Saffron: a potential candidate for a novel anticancer drug against hepatocellular carcinoma", Hepatology Malignancies, 2011, vol. 54, No. 3, pp. 857-867, 11 pages.
Apel et al., "Phenanthrene derivatives from Appendicula reflexa as new CDK1/cyclin B inhibitors", Elsevier, Phytochemistry Letters, 2012, vol. 5, No. 4, pp. 814-818, 5 pages.
Bi, et al., "Identification of Caspase-6 and Caspase-7 from miiuy croaker and evolution analysis in fish", Elsevier, Fish & Shellfish Immunology, Science Direct, 2018, vol. 83, pp. 406-409, 4 pages.
Chaitanya et al., "PARP-1 cleavage fragments: signatures of cell-death proteases in neurodegeneration", Cell Communication and Signaling, 2014, vol. 8, No. 31, 11 pages.
Crissien & Frenette, "Current Management of Hepatocellular Carcinoma", Gastroenterology & Hepatology, 2014, vol. 10, No. 3, pp. 153-161, 9 pages.
Fanale et al., "Stabilizing versus destabilizing the microtubules: a double-edge sword for an effective cancer treatment option?", Review Article, Analytical Cellular Pathology, 2015, vol. 2015, 19 pages.
Ferlay et al., "Cancer incidence and mortality worldwide: Sources, methods and major patterns in GLOBOCAN 2012", International Journal of Cancer, 2012, vol. 136, No. 5, pp. E359-E386, 28 pages.
Finn et al., "Phase I study investigating everolimus combined with sorafenib in patients with advanced hepatocellular carcinoma", Journal of Hepatology, vol. 59, No. 6, pp. 1271-1277, 7 pages.
Fischer,et al., "Hematoxylin and eosin staining of tissue and cell sections", CSH Protocols, 2008, vol. 3, No. 5, 3 pages.
Gardino & Yaffe, "14-3-3 proteins as signaling integration points for cell cycle control and apoptosis", Seminars in Cell & Developmental Biology, 2011, vol. 22, No. 7, pp. 688-695, 18 pages.
Gohari et al., "An overview on saffron, phytochemicals, and medicinal properties", Pharmacognosy Reviews, vol. 7, No. 13, pp. 61-66, 7 pages.
Greenwell & Rahman, "Medicinal Plants: Their Use in Anticancer Treatment", International Journal of Pharmaceutical Sciences and Research, 2015, vol. 6, No. 10, pp. 4103-4112, 13 pages.
Hamza et al., "Molecular characterization of the grape seeds extract's effect against chemically induced liver cancer: In vivo and in vitro analyses", Scientific Reports, 2018, vol. 8 No. 1270, 16 pages.
Hanahan & Weinberg, "Hallmarks of Cancer: The Next Generation" Elsevier, Inc. Cell, 2011, vol. 144, No. 05, pp. 646-674, 29 pages.
Hassan et al., "Cape gooseberry (*Physalis peruviana*) juice as a modulator agent for hepatocellular carcinoma-linked apoptosis and cell cycle arrest", Elsevier, Science Direct, Biomedicine & Pharmacotherapy, 2017, vol. 94, pp. 1129-1137, 10 pages.
Hosseinzadeh et al., "Acute and Subacute Toxicity of Safranal, a Constituent of Saffron, in Mice and Rats", Iranian Journal of Pharmaceutical Research : IJPR, 2013, vol. 12, No. 1, pp. 93-99, 7 pages.
Hu et al., Common housekeeping proteins are upregulated in colorectal adenocarcinoma and hepatocellular carcinoma, making the total protein a better "housekeeper" Oncotarget, 2016, vol. 7, No. 41, pp. 66679-66688, 10 pages.
Hübscher, "Histological assessment of the liver", Elsevier Ltd., Medicine, vol. 43, No. 10, pp. 568-572, 5 pages.
Juriková et al., "Ki67, PCNA, and MCM proteins: Markers of proliferation in the diagnosis of breast cancer", Elsevier, Acta Histochemica, 2016,vol. 118, No. 5, pp. 544-552, 9 pages.
Karafakioğlu et al., "Efficacy of safranal to cisplatin-induced nephrotoxicity", Portland Press, The Biochemical Journal Accepted Manuscript, 2017, vol. 474, No. 7, pp. 1195-1203, 27 pages.
Kesharwani et al., "Multifunctional approaches utilizing polymeric micelles to circumvent multidrug resistant tumors", Elsevier, Colloids and Surfaces B: Biointerfaces, 2019, vol. 173, pp. 581-590, 10 pages.
Kim & Kim, "Selection of optimal internal controls for gene expression profiling of liver disease", BioTechniques, 2003, vol. 35, No. 3, pp. 456-460, 3 pages.
Kmieć, "Cooperation of liver cells in health and disease", Advances in Anatomy, Embryology, and Cell Biology, 2001. vol. 161, III-XIII, 1-151,1 page.
Lee et al., "Roles of Bcl-2 and caspase-9 and -3 in CD30-induced human eosinophil apoptosis", Science Direct, Journal of Microbiology, Immunology and Infection, 2017, vol. 50, No. 2, pp. 145-152, 8 pages.
Li et al., "PSAP induces a unique Apaf-1 and Smac-dependent mitochondrial apoptotic pathway independent of Bcl-2 family proteins", _Biochim Biophys Acta (BBA)—Molecular Basis of Disease, 1832(3), 453-474.
Li et al., "Synthesis and biological evaluation of novel thiadiazole amides as potent Cdc25B and PTP1B inhibitors", Elsevier, Bioorganic & Medicinal Chemistry Letters, 2014, vol. 24, No. 17, pp. 4125-4128, 4 pages.
Liu et al., "Distinct pro-apoptotic properties of Zhejiang saffron against human lung cancer via a caspase-8-9-3 cascade", Research Article, Asian Pacific Journal of Cancer Prevention: APJCP, vol. 15, No. 15, pp. 6075-6080, 6 pages.
Liu et al., "Nitrogen-containing flavonoids as CDK1/Cyclin B inhibitors: Design, synthesis, and biological evaluation", Elsevier, Science Direct, Bioorganic & Medicinal Chemistry Letters, 2007, vol. 17, ,No. 1, pp. 278-281, 4 pages.
Llovet et al., "Sorafenib in Advanced Hepatocellular Carcinoma", SHARP Investigators Study Group, The New England Journal of Medicine, 2008, vol. 359, No. 4, pp. 378-390, 13 pages.
Los et al., "Activation and Caspase-mediated Inhibition of PARP: A Molecular Switch between Fibroblast Necrosis and Apoptosis in Death Receptor Signaling", Molecular Biology of the Cell, 2002, vol. 13, No. 3, pp. 978-988, 11 pages.
Lui, "Laboratory tests in liver failure", Clinical Assessment, Royal College of Anaesthetists CPD Matrix: 1A03, Elsevier, Anaesthesia & Intensive Care Medicine, 2017, vol. 19, No. 1, pp. 1-3, 3 pages.

\* cited by examiner

| Species | Reference body weight (kg) | Working weight range (kg) | Body surface area (m²) | To convert dose in mg/kg to dose in mg/m², multiply by $K_m$ | To convert animal dose in mg/kg to HED in mg/kg, either | |
|---|---|---|---|---|---|---|
| | | | | | Divide animal dose by | Multiply animal dose by |
| Human | 60 | · | 1.62 | 37 | · | · |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 13

SAFRANAL-SORAFENIB COMBINATION THERAPY FOR LIVER CANCER

TECHNICAL FIELD

The present invention relates to therapeutic formulations and methods for treating liver cancer including safranal and sorafenib.

BACKGROUND

Despite all efforts, more people are diagnosed with hepatocellular carcinoma (HCC); the most common type of primary liver cancer and the second leading cause of cancer-related death worldwide. Multiple risk factors contribute to HCC development including chronic hepatitis (B and C) infection that accounts for 70%-90% of HCC cases by providing a permissive environment for HCC development. Other HCC risk factors include alcoholism, non-alcohol fatty liver disease, iron overload, and environmental carcinogens. Early stages of HCC show no symptoms, thus most patients are diagnosed at advanced stages. In addition, HCC exhibits a high rate of recurrence after resection or ablation; and is considerably resistant to cytotoxic chemotherapy, with a very limited number of available treatments. Thus, alternative therapeutics are well justified and are desperately needed to treat HCC.

Chemotherapy is the most common treatment of cancer patients. HCC is however, chemo-resistant, and the side-effects of chemotherapy are typically exhausting to the patient. Sorafenib is the first anti-HCC drug approved by the U.S. Food and Drug Administration. It is a multikinase inhibitor that blocks tumor cells proliferation and angiogenesis. Although sorafenib is successful in treating early and mid HCC lesions, it is not efficient in advanced HCC cases. The common side effects of sorafenib are skin toxicity, diarrhea, hypertension, and bleeding.

Natural products have long been a part of folk medicine and have been playing an instrumental role in the development of anti-cancer drugs. Thanks to their nontoxicity and low-to-no associated side effects, 40% of FDA-approved therapeutic agents are natural-based components or their derivatives. Considering their great efficacy and low toxicity, natural products have been extensively studied and introduced as a chemopreventive therapy for many diseases including cancer. Medicinal plants have been suggested for cancer prevention and therapy for several reasons; they contain nutritional and anti-tumor compounds, are able to delay or prevent cancer onset, can boost the physiological status and the immune system, and most importantly, they represent a great alternative and/or adjuvant option to conventional cancer treatments by alleviating or even averting their side effects.

Saffron (the stigmas of the flower of *Crocus sativus*), is increasingly gaining attention as it contains many bioactive molecules with health promoting properties; including crocin, crocetin, picrocrocin, and safranal, Previous studies have reported the anti-cancer activity of saffron and its derivatives against a wide range of cancers. While saffron's derivatives have been reported to inhibit the growth of HeLa cells, safranal has specifically been shown to exert potent anti-inflammatory, antioxidant and anti-cancer properties and was found to induce apoptosis in both alveolar human lung cancer A549, and human prostate cancer PC-3 cell lines. Despite all its anti-tumor activities, the mechanism through which safranal exerts its anti-cancer effect is yet to be fully understood.

Hence, it would be advantageous to understand the mechanism through which safranal exerts anti-cancer effects so it may be developed into an effective treatment for liver and other cancer types, either alone or in combination with chemotherapeutical agents.

SUMMARY OF THE EMBODIMENTS

In accordance with a first aspect of the invention, the present application provides a therapeutic combination of drugs for the treatment of a liver cancer. The combination includes: safranal or a pharmaceutically acceptable pro-drug thereof, and sorafenib. In representative embodiments, the pro-drug is selected from the group consisting of a safranal salt, hydrate, hemiacetal, acetal, thioacetal, silylether, tautomer, isomer, and combinations thereof. The safranal and the sorafenib may be compounded together in a same unitary pharmaceutical composition including both compounds. Alternatively, the safranal and the sorafenib may be provided in the form of separate pharmaceutical compositions.

In accordance with a second aspect of the invention, the present application provides a method of treating, suppressing, or reducing the severity of a liver cancer in a subject. The method includes administering to the subject the therapeutic combination of safranal and sorafenib. In representative embodiments, the liver cancer is selected from the group consisting of hepatocellular carcinoma (HCC), fibrolamellar HCC, cholangiocarcinoma, angiosarcoma, a metastatic liver cancer, and combinations thereof. In an embodiment, the mass-to-mass ratio of safranal:sorafenib administered to the subject is in the range of about 50:1 to about 1:1. In a further embodiment, the mass-to-mass ratio of safranal:sorafenib administered to the subject is in the range of about 25:1 to about 1:1. In exemplary embodiments, the mass-to-mass ratio of safranal:sorafenib is based on the respective amounts of safranal and sorafenib administered to the subject in a single day, a single week, 14 days, 21 days, or 28 days. In an embodiment, the amount of the safranal or pro-drug thereof is from about 10 mg/day to about 1000 mg/day per kg body weight of the subject. In a further embodiment, the amount of the safranal or pro-drug thereof is from about 200 mg/day to about 750 mg/day per kg body weight of the subject. In an additional embodiment, the amount of the safranal or pro-drug thereof is from about 250 mg/day to about 500 mg/day per kg body weight of the subject. The safranal may be administered to the subject prior to the sorafenib, concurrently with the sorafenib, or after the sorafenib. In an embodiment, the sorafenib is administered to the subject in an amount of about 800, 600, 400, or 200 mg/day. In a further embodiment, the sorafenib is administered at an effective dose that is at least 50% to at most 90% or more below the dose needed to be effective in the absence of safranal administration. The liver cancer may have primary or secondary resistance to sorafenib.

In accordance with a third aspect of the invention, the present application provides a kit for the treatment of liver cancer. The kit includes a first pharmaceutically acceptable composition of safranal, a second pharmaceutical composition of sorafenib, and instructions for the administration of the first composition and second composition for treatment of liver cancer. In representative embodiments, the liver cancer is selected from the group consisting of hepatocellular carcinoma (HCC), fibrolamellar HCC, cholangiocarcinoma, angiosarcoma, a metastatic liver cancer, and combinations thereof.

BRIEF DESCRIPTION OF THE FIGURES

The invention can be better understood with reference to the following figures and description. The components in the figures are not necessarily to scale and are not intended to accurately represent molecules, cells, cell organelles, tissues, or their interactions, emphasis instead being placed upon illustrating the principles of the invention.

FIG. 7A is a western blot analysis of the proliferation-related protein (PCNA) on DEN-induced hepatic neoplasia in rats untreated (HCC group) or treated with sorafenib (HCC SB), safranal (HCC SF) individually or combined (HCC SF+SB).

FIG. 7B reports the quantification of each band intensity from FIG. 7A. Quantification was carried out using ImageJ, normalized in relative to the total protein from the liver.

FIG. 13 is a table reporting human equivalent dose (HED) dosage factors based on body surface area of other species according to data obtained from Food and Drug Administration draft guidelines.

DETAILED DESCRIPTION OF SPECIFIC EMBODIMENTS

Figure 1:
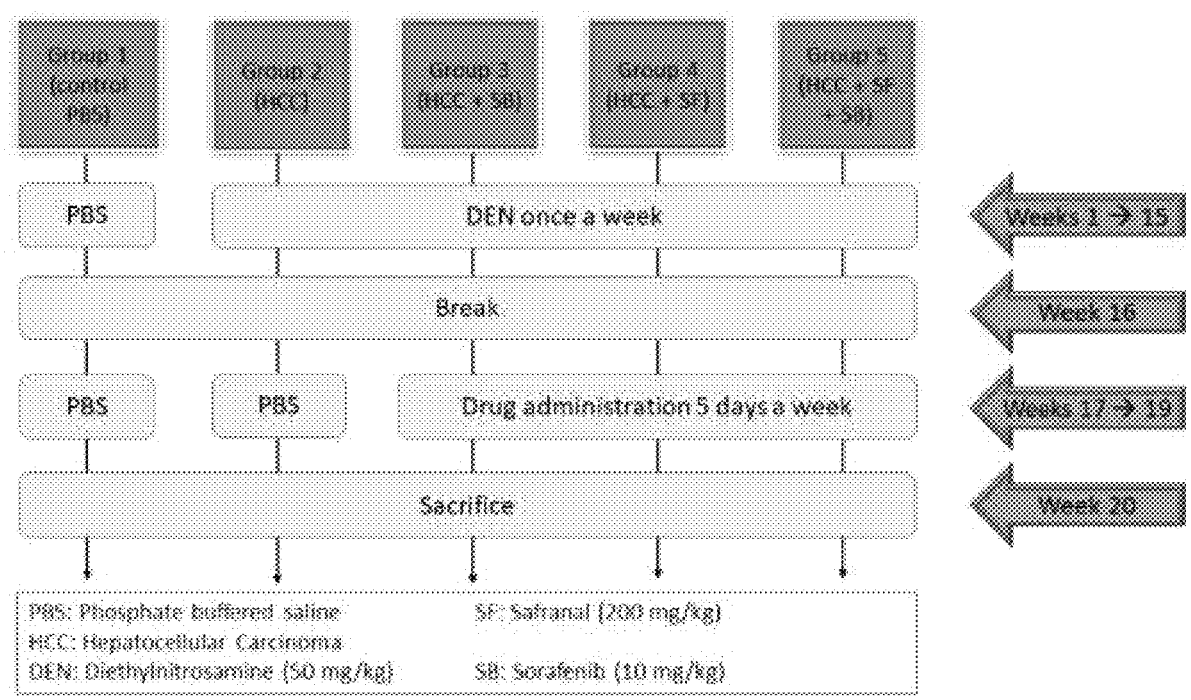
FIG. 1 provides the experimental design of an in vivo study conducted to establish a hepatocarcinogenesis model.

The present invention is at least in part based on the finding that safranal and sorafenib exert a synergistic anti-cancer effect on HCC in laboratory rats. This therapeutic effect can be put to use in the treatment of liver cancer. Compared with monotherapy with sorafenib alone, treatment with safranal in combination with sorafenib targeting multiple signaling pathways offers a better treatment alternative potentially abolishing resistance, feedback activation, and compensatory activation of survival pathways. Without being bound to any particular theory, it is believed that safranal may sensitize hepatic cells to sorafenib's effect by further decreasing the expression of cell cycle-related proteins than sorafenib alone. This finding can be described as a synergy, or greater than additive effect, that is specific to certain combinations of sorafenib and safranal, and liver cancer, with a higher improvement than with monotherapy with sorafenib.

In exemplary embodiments, provided herein are therapeutic combinations of drugs including a first amount of safranal (or its pharmaceutically acceptable pro-drug) and a second amount of sorafenib. Essentially, the combination of safranal and sorafenib represents a therapeutic combination that may be more efficacious than either agent alone or the simple sum of the two agents. In addition, different doses of the combination may lead to additional gains in treatment of the liver cancer than either safranal or sorafenib alone. Accordingly, in some embodiments, the present application provides unexpectedly advantageous methods and compositions for treating liver cancer, whereby sorafenib and a safranal are administered in a ratio that is particularly effective (e.g., synergistic or more than additive).

Safranal

In several embodiments, the present invention includes the use of safranal. Safranal is a molecule having the IUPAC name 2,6,6-trimethyl-1,3-cyclohexadiene-1-carboxaldehyde and its structural formula is:

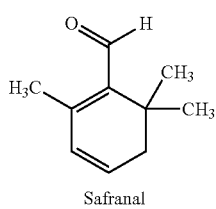

Safranal

Formula I

Safranal includes an alpha, beta, gamma, delta-unsaturated aldehyde group and is therefore capable of forming hemiacetals, acetals, thioketals, silyl ethers, and other derivatives resulting from nucleophilic addition reactions to the beta- or delta-carbon of the unsaturation. In instances where the safranal derivatives are pharmaceutically acceptable and easily cleavable under physiological conditions, one or more derivative may be administered to the patient as a pro-drug of safranal itself. The term "pharmaceutically acceptable safranal derivative", in this respect, refers to the pharmaceutically acceptable and easily cleavable groups of safranal, including hemiacetals, acetals, thioketals, silyl ethers, and nucleophilic addition products. These pro-drugs can be prepared in situ in the administration vehicle or in the dosage form manufacturing process, or by separately reacting safranal with a suitable reactant, and isolating the derivative thus formed during subsequent purification. Other derivatives that may serve as pro-drugs include pharmaceutically acceptable salts and hydrates. Therapeutically effective tautomers and isomers of safranal are also contemplated. Unless otherwise specified, the terms "composition including safranal" and "formulation of safranal" as used herein are intended to cover compositions and formulations including safranal itself, its pro-drugs such as pharmaceutically acceptable hemiacetals and acetals, pharmaceutically acceptable tautomers and isomers, and pharmaceutically acceptable salts thereof.

A composition including safranal may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of safranal include those suitable for parenteral (including subcutaneous, intravenous, intramedullary, intraarticular, intramuscular, or intraperitoneal injection), rectal, topical, transdermal, or oral (for example, in capsules, suspensions, or tablets) administration. The formulations may conveniently be presented in unit dosage form and may be prepared by any methods well known in the art of pharmacy. The amount of safranal or its pharmaceutically acceptable pro-drugs which can be combined with a carrier material to produce a single dosage form will vary depending upon the subject being treated and the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

Regardless of the route of administration selected, safranal or its pro-drugs may be formulated into pharmaceutically-acceptable dosage forms by conventional methods known to those of skill in the art. Safranal may be formulated for administration in any convenient way for use in human or veterinary medicine, by analogy with other pharmaceuticals.

Sorafenib

In various embodiments, the present invention includes the use of sorafenib, for example in the form of sorafenib tosylate as well as other pharmaceutically acceptable forms, salts, and esters of sorafenib. Sorafenib is commercially available as NEXAVAR®, which is the tosylate salt of sorafenib. Sorafenib tosylate has IUPAC chemical name 4-(4-{3-[4-Chloro-3 (trifluoromethyl)phenyl]ureido} phenoxy) N-methylpyridine-2-carboxamide 4-methylbenzenesulfonate and its structural formula is:

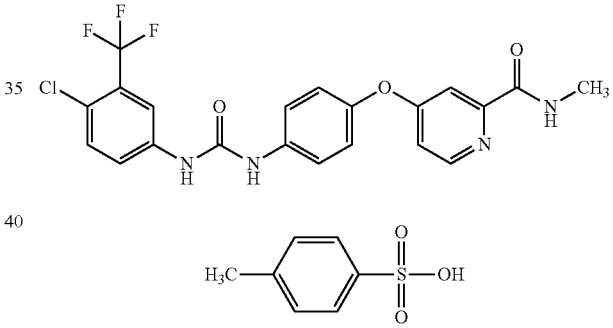

Formula II

The recommended daily dose of sorafenib tosylate is 800 mg administered as 400 mg (two tablets) orally twice daily. However, treatment interruption and/or dose reduction may be needed to manage suspected adverse drug reactions. In such instances, the dose may be reduced to 400 mg once daily or to 400 mg every other day. A person of ordinary skill will understand that sorafenib dosage and administration can follow medically approved guidelines, as well medically accepted deviations or alterations to such guidelines.

Liver Cancer

In one aspect, the present invention provides methods for the treatment of liver cancer cells, including cancer cells in a subject or in vitro treatment of isolated cancer cells. If the cancer cells are in a subject, the subject may be a primate, such as a human, with liver cancer. The subject may be a mammal. The subject may be an adult human (i.e., 18 years or older), or a juvenile human (i.e., less than 18 years old). In various embodiments, the liver cancer may be a hepatocellular carcinoma (HCC), a fibrolamellar HCC, a cholangiocarcinoma, an angiosarcoma, or a metastatic liver cancer.

In some embodiments, the liver cancer is not resistant to sorafenib. Alternatively, the liver cancer may have primary or secondary resistance to sorafenib. The subject can be a responder to sorafenib in the absence of the safranal. The subject can be a non-responder to sorafenib in the absence of safranal. In some embodiments, the subject has undergone a prior treatment with sorafenib lasting at least 1, 2, 4, 6, 8, 10 months or longer. In other embodiments, the subjects are patients who have experienced one or more significant adverse side effect to sorafenib and therefore require a reduction in dose.

In some embodiments, the liver cancer is intermediate, advanced, or terminal stage. The liver cancer can be metastatic or non-metastatic. The liver cancer may be resectable or unresectable. The liver cancer may include a single tumor, multiple tumors, or a poorly defined tumor with an infiltrative growth pattern (into portal veins or hepatic veins). The liver cancer may include a fibrolamellar, pseudoglandular (adenoid), pleomorphic (giant cell), or clear cell pattern. The liver cancer may include a well differentiated form, and tumor cells resemble hepatocytes, form trabeculae, cords, and nests, and/or contain bile pigment in cytoplasm. The liver cancer may include a poorly differentiated form, and malignant epithelial cells are discohesive, pleomorphic, anaplastic, and/or giant. In some embodiments, the liver cancer may be associated with hepatits B, hepatitis C, cirhhosis, or type 2 diabetes.

In some embodiments, the subject is a human having an Eastern Cooperative Oncology Group (ECOG) performance status ≤2. In some embodiments, the subject is a human having acceptable liver function defined as (i) total bilirubin ≤1.5 times the upper limit of normal (ULN); for patients with hepatocellular carcinoma only, total bilirubin ≤3 mg/dL (i.e., Child-Pugh Score for bilirubin is no greater than 2); (ii) aspartate aminotransferase (AST), alanine aminotransferase (ALT) and alkaline phosphatase (ALP) ≤5×ULN; or (iii) acceptable renal function: Serum creatinine ≤1.5 times the ULN, or calculated creatinine clearance ≥60 mL/min/1.73 m$^2$ for patients with creatinine levels above 1.5 times the institutional normal.

In some embodiments, the subject is a human having acceptable hematological status defined as (i) absolute Neutrophil Count (ANC) ≥1500 cells/mm$^3$; (ii) platelet count ≥100,000 plts/mm$^3$ (without transfusion); ≥75,000 pits/mm$^3$ for patients with hepatocellular carcinoma only; or (iii) hemoglobin ≥9 g/dL.

In some embodiments, the subject is a human having a prothrombin time (PT) or International Normalized Ratio (INR) ≤1.25×ULN; INR <1.7 or prothrombin time (PT) or <4 seconds above ULN (i.e., Child-Pugh Score is no greater than 1 for the coagulation parameter); or serum albumin >2.8 g/dL (i.e., Child-Pugh Score for albumin is no greater than 2).

Combination Therapy

Combination therapy or polytherapy is the use of more than one medication or other therapy, as opposed to monotherapy, which is any therapy taken alone. In one aspect of the present invention, provided herein is a therapeutic combination of drugs for the treatment of liver cancer, the combination including safranal and sorafenib. In an example embodiment of the combination, the safranal and sorafenib are compounded together in a same unitary pharmaceutical composition including both compounds. In another example embodiment, the safranal and sorafenib are in separate pharmaceutical compositions. Also provided are methods for treating, suppressing, or reducing the severity of a liver cancer in a subject by administering to the subject a therapeutic amount of the combination.

In some embodiments, the therapeutic combination refers to using specific combinations (e.g., ratios and/or dosing schedules) of safranal and sorafenib. More particularly, the invention provides therapeutic combinations and methods for treating liver cancer where the safranal and sorafenib are administered in a ratio that is particularly effective (e.g., synergistic or more than additive). In representative embodiments, the ratio, that is, the mass-to-mass ratio of safranal: sorafenib is about 50 to 1, 40 to 1, 30 to 1, 25 to 1, 20 to 1, 10 to 1, 5 to 1, 2 to 1, 1 to 2, 1 to 5, 1 to 10, 1 to 20, 1 to 30, 1 to 40, or 1 to 50. In some embodiments, the ratio is, or is at least, about 1, 2, 5, 10, 12, 15, 20, or 50. In some embodiments, the ratio is less than about 5, 10, 15, 20, 30, 40, 50, 60, or 70. Example weight-to-weight ratios are about 1, 2, 5, 8, 10, 15, 20, 25, 30, 40, and 50.

The mass-to-mass ratio of safranal:sorafenib can be measured over different periods of time. For example, the mass ratio may be based on the respective amounts of safranal and sorafenib administered to the subject in a single day, a single week, 14 days, 21 days, or 28 days.

The sorafenib dosing amount and/or schedule can follow clinically approved, or experimental, guidelines. In various embodiments, the dose of sorafenib is about 800, 600, 400, or 200 mg/day. A 200 mg/day dose can be administered as a 400 mg dose every other day.

Likewise the safranal dosing amount and/or schedule can follow clinically approved, or experimental, guidelines. Also, the data obtained from animal studies may be used in formulating a safranal range of dosage for use in humans. For example, effective dosages achieved in one animal species may be extrapolated for use in another animal, including humans, as illustrated in the conversion table of FIG. 13 where human equivalent dose (HED) dosage factors based on body surface area of other species are reported. (Nair and Jacob, 2016). In exemplary embodiments, the dose of safranal fall in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of safranal will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg to about 250 mg per kg/day. In a further embodiment, the dose in the range of about 100 mg to about 200 mg per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The dose of safranal can be set, within a therapeutically effective range, based upon a selected ratio and dose of sorafenib. As discussed above, the ratio can be determined using the amount of sorafenib administered to a subject over a single day, a single week, 14 days, 21 days, or 28 days.

In some embodiments, the safranal is administered to the subject in 1, 2, 3, 4, 5, 6, or 7 daily doses over a single week (7 days). The safranal may be administered to the subject in 1, 2, 3, 4, 5, 6, 7, 8, 9, 10, 11, 12, 13, or 14 daily doses over 14 days. The safranal may be administered to the subject in 1, 2, 3, 4, 5, 6, 7, 8, 9, 10, 11, 12, 13, 14, 15, 16, 17, 18, 19, 20, or 21 daily doses over 21 days. The safranal may be administered to the subject in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In various embodiments, the safranal is administered for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); 1 week with 3 consecutive weeks off (total 28 days).

In further embodiments, the safranal is: administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. The safranal can be administered once every 1, 2, 3, 4, 5, 6, 7, or 8 weeks.

A course of safranal-sorafenib therapy can be continued until a clinical endpoint is met. In some embodiments, the therapy is continued until disease progression or unacceptable toxicity occurs. In some embodiments, the therapy is continued until achieving a pathological complete response rate defined as the absence of liver cancer (e.g., HCC). In some embodiments, the therapy is continued until partial or complete remission of the liver cancer. Administering the safranal and the sorafenib to a plurality of subject having liver cancer may increase the Overall Survival (OS), the Progression free Survival (PFS), the Disease Free Survival (DFS), the Response Rate (RR), the Quality of Life (QoL), or a combination thereof.

In various embodiments, the treatment reduces the size and/or number of the liver cancer tumor(s). The treatment can prevent the liver cancer tumor(s) from increasing in size and/or number. The treatment can prevent the liver cancer tumor(s) from metastasizing.

In the methods of the invention, administration of the safranal and sorafenib is not limited to any particular delivery system and may include, without limitation, one or more of parenteral (including subcutaneous, intravenous, intramedullary, intraarticular, intramuscular, or intraperitoneal injection), rectal, topical, transdermal, or oral (for example, in capsules, suspensions, or tablets). Administration to an individual may occur in a single dose or in repeat administrations, and in any of a variety of physiologically acceptable pro-drug or salt forms, and/or with an acceptable pharmaceutical carrier and/or additive as part of a pharmaceutical composition. Physiologically acceptable salt forms and standard pharmaceutical formulation techniques, dosages, and excipients are well known to persons skilled in the art. Additionally, effective dosages achieved in one animal may be extrapolated for use in another animal, including humans, using conversion factors known in the art.

The combination therapies of the invention are not specifically limited to any particular course or regimen and may be employed separately or in conjunction with other therapeutic modalities (e.g., chemotherapy or radiotherapy).

In some embodiments, the safranal is administered prior to the sorafenib, concurrently with the sorafenib, after the sorafenib, or a combination thereof. The safranal may be administered systemically or regionally.

A combination therapy in accordance with the present invention can include additional therapies (e.g., pharmaceutical, radiation, and the like) beyond the safranal and sorafenib. Similarly, the present invention can be used as an adjuvant therapy (e.g., when combined with surgery). In various embodiments, the subject is also treated by surgical resection, percutaneous ethanol or acetic acid injection, transcatheter arterial chemoembolization, radiofrequency ablation, laser ablation, cryoablation, focused external beam radiation stereotactic radiotherapy, selective internal radiation therapy, intra-arterial iodine-131-lipiodol administration, and/or high intensity focused ultrasound.

The combination of the safranal and sorafenib can be used as an adjuvant, neoadjuvant, concomitant, concurrent, or palliative therapy. The combination of the safranal and sorafenib can be used as a first line therapy, second line therapy, or crossover therapy.

In some embodiments, the therapeutically effective dose of sorafenib is reduced through combination with safranal. For example, the daily, weekly or monthly dose of sorafenib can be reduced by at least 10%, 20%, 30%, 40%, 50%, 60%, 70%, 80%, 90% or more relative to the maximum recommended dose or the maximum tolerated dose. In other embodiments, sorafenib is administered at an effective dose that is at least 30%, 40%, 50%, 60%, 70%, 80%, 90% or more below the dose needed to be effective in the absence of safranal administration. In some embodiments, the IC50 of sorafenib is reduced by at least 2-, 4-, 5-, 10-, 20-, 30-, 40-, 50-, or 100-fold relative to the IC50 in the absence of safranal.

Kits

The present invention also provides kits for treating liver cancer. For example, a kit may include one or more pharmaceutical compositions of safranal and sorafenib as described above. The compositions may be pharmaceutical compositions comprising a pharmaceutically acceptable excipient. In other embodiments involving kits, there is provided a kit including a first pharmaceutically acceptable composition including safranal, a second pharmaceutically acceptable composition including sorafenib, and optionally instructions for their use in the treatment of liver cancer. In still other embodiments, there is provided a kit including one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter.

Experimental Results

In vivo HCC model was successfully induced in male Wistar rats, then treated with sorafenib alone, safranal alone, and with both safranal and sorafenib. Data analysis showed the efficiency of safranal as a drug and an adjuvant in restoring liver function. Presented results also showed safranal's inhibitory role of cell cycle, and its proapoptotic capacity suggesting safranal's high potential as a novel anti-cancer drug.

Male Wistar rats, weighing around 160 gm, were used in this study. Rats were provided by the animal research facility at the College of Medicine and Health Sciences, United Arab Emirates University. Rats were housed under a 12-hour light/dark cycle at 24-26° C. They were maintained on a standard laboratory animal diet with food and water ad libitum.

Experimental Design

A modified version of the protocol described by DePeralta et al. (2016) and Schiffer et al. (2005) was used here to establish the hepatocarcinogenesis model. As seen in FIG. 1, animals were divided into five groups, each group having eight animals labelled as follows: control phosphate buffered saline (PBS), HCC, HCC+sorafenib, HCC+safranal, and HCC+safranal+sorafenib.

On the first 15 weeks, the control PBS group was treated with 1×PBS, whereas the experimental groups were given an intraperitoneal injection (IP) of 50 mg/kg of diethylnitrosoamine (DEN, Sigma Aldrich), a widely used chemical for inducing cancer, once a week. DEN was diluted with 1×PBS. Following a one-week break (week 16), the next three weeks (weeks 17 to 19) of treatment commenced. All drugs were administrated by oral gavage. All doses were chosen according to literature (Alsaied et al., 2014; Karafakioğlu et al., 2017). For the HCC+sorafenib group, the drug (Carbosynth Limited) was administered at a dose of 10 mg/kg, five days a week. For the HCC+safranal group, the drug (Sigma Aldrich) was administered at a dose of 200 mg/kg, five days a week. For the HCC+safranal+sorafenib group, the drugs were administered at a dose of 200 mg/kg safranal+10 mg/kg sorafenib, five days a week. Both safranal and sorafenib were diluted with 1×PBS and drops of Tween 80. The oral $LD_{50}$ of safranal is 5.53 mL/kg in male rats (Hosseinzadeh et al., 2013). After 24-hours from last treatment, the rats were euthanized by mild diethyl ether and dissected in equal conditions. Blood and whole liver were collected.

Blood Samples

Rats were euthanized then blood was collected by decapitation and processed for later investigation. The blood was collected in collection tubes (BD Vacutainer) and serum was separated by centrifugation at 1200×g for 10 minutes. Serum was collected and flash frozen immediately then stored at −80° C. for further analysis.

Biochemical Analysis

Alanine Transaminase (ALT), and Aspartate Aminotransferase (AST) assays were performed using commercial kits (Abcam), according to the protocol provided. ALT and AST activities were measured spectrophotometrically using Epoch by BioTek.

Liver Samples

Part of the liver was immediately flash frozen in liquid nitrogen then stored at −80° C. for further analysis. The other part was kept in 10% neutral buffered formalin at room temperature for histology.

Histopathological Examination

Liver sample specimens were fixed in 10% neutral buffered formalin, dehydrated in a series of graded ethanol, embedded in paraffin blocks, and cut into 3 μm-thick sections. To detect histopathological changes, sections were stained with hematoxylin and eosin (H&E), and reticulin stain kit according to the protocol provided (Abcam), then examined under light microscope (Ozkececi et al., 2016). Blinded examination of tissue samples was carried out by a pathologist from Tawam Hospital—United Arab Emirates.

Western Blotting

One hundredth gm (10 mg) liver was homogenized using 200 μl RIPA buffer (Sigma Aldrich) mixed with 2 μl protease inhibitor and 2 μl phosphatase inhibitor (Sigma Aldrich), and centrifuged at 4° C., 15,000 rpm for 15 minutes. Whole cell lysate was taken and stored at −80° C. Protein concentration was measured by Pierce BCA Protein Assay Kit with Promega GloMax Discover. A total of 35 μg of protein was loaded on a sodium dodecyl sulfate-polyacrylamide gel electrophoresis gel. The gel was then transferred to polyvinylidene difluoride membrane. The membrane was then blocked with 5% BSA in TBST for one hour at room temperature. Membranes were incubated with anti-Proliferating Cell Nuclear Antigen (PCNA), anti-PolyADP-ribose Polymerase (PARP), anti-caspase-3 (Cell Signaling Technology Inc.), anti-caspase-9 (Novus Biologicals), anti-Bax, anti-Bcl-2 (Santa Cruz), anti-Cdk1, anti-Cyclin B1, anti-Cdc25B (Cell Signaling Technology Inc.) over night at 4° C., then with HRP conjugated secondary, anti-mouse or anti-rabbit, antibody (Cell Signaling Technology Inc.) for one hour at room temperature. All primary and secondary antibodies were diluted in 5% BSA in TBST. Blots were incubated in WesternSure PREMIUM Chemiluminescent Substrate for antibodies' detection. Signal was visualized using Bio-Rad ChemiDoc XRS+ System. Band density and quantification was done using ImageJ (Amin et al., 2011). Total protein was used as a loading control and stained using SYPRO Ruby protein gel stain according to the protocol provided (Thermo Fisher Scientific) (Aldridge et al., 2008; Hu et al., 2016).

Total Protein as a Loading Control

Due to technical reasons, total protein was used in this study as the loading control instead of the other common markers like GAPDH, β-tubulin, and β-actin. A study published in 2003 used liver samples from normal, cirrhotic, and HCC tissues to inspect the housekeeping genes. Ten internal controls were used, and their expressions were determined using RT-PCR. Results showed that all internal control genes varied more than a 2-fold, and the commonly used genes like GAPDH and β-actin varied from 7- to 23-fold, precisely in tumor tissue (Kim & Kim, 2003). Following studies then tried to find an alternative way for this issue. Total protein, depending on the amount of total protein rather than a single protein, served as a better control for colorectal cancer and HCC compared with different common housekeeping proteins. Also, testing the signal's linearity with the loading amounts was preserved in total protein, while in the other housekeeping proteins it was lost (Aldridge et al., 2008; Hu et al., 2016). Due to technical problems with all common internal controls, a protocol that was mentioned by Aldridge et al. (2008) and Hu et al. (2016) was followed.

Results

Several enzymes are released from hepatocytes into the blood and are measured in the blood serum to test the efficiency of liver function, ALT and AST are the most common enzymes. The more severe the liver is damaged, the higher their serum levels get. Together, they are considered the best markers for liver injury (Liu et al., 2012). In addition to serum, the whole liver tissues were collected and properly stored for further histological and immunoblotting analyses. In histological examination, liver tissues were processed and stained for final imaging using the microscope (Martin, 2015). To detect markers of specific pathways, selected proteins were targeted using western blotting.

Biochemical Analysis

As shown in Table 1, ALT ($P<0.05$) and AST levels were elevated in HCC group as compared to control group, thus indicating liver damage. Treatment with safranal and with both safranal+sorafenib significantly ($P<0.05$) decreased ALT levels in the treated groups as compared to HCC group. Safranal and the combination therapy caused a significance decrease ($P<0.05$) as compared to sorafenib alone (HCC+sorafenib). Values are expressed as mean±SEM of six rats per group (n=6). Activity is expressed as mU/ml for ALT and AST. Significance was determined by one-way ANOVA followed by Tukey's post hoc analysis (a versus PBS, b versus HCC, c versus HCC+Sorafenib; $P<0.05$).

TABLE 1

|  | Control PBS | HCC | HCC + sorafenib | HCC + safranal | HCC + safranal + sorafenib |
|---|---|---|---|---|---|
| ALT | 7.76 ± 0.38 | 14.10 ± 0.15$^{a*}$ | 13.42 ± 0.22 | 10.93 ± 0.29$^{b*,c*}$ | 9.55 ± 0.61$^{b*,c*}$ |
| AST | 9.00 ± 0.39 | 10.18 ± 1.69 | 11.14 ± 0.62 | 7.80 ± 2.02 | 10.98 ± 0.50 |

As the results show in Table 1, treatment with safranal decreased the elevation of ALT comparing to HCC group (P<0.05) with a higher efficiency of safranal alone and the synergic group (HCC+safranal+sorafenib) over sorafenib alone (P<0.05). This highlights the efficiency of safranal and its potential in combination therapy. The insignificant change of AST can be explained as ALT is more diagnostic enzyme found exclusively in the liver, while AST is not just found in the liver, but also in the muscles. AST is also cleared from the liver twice as fast as ALT, therefore ALT level is increased more than AST after liver injury (Lui, 2018).

Figure 2:
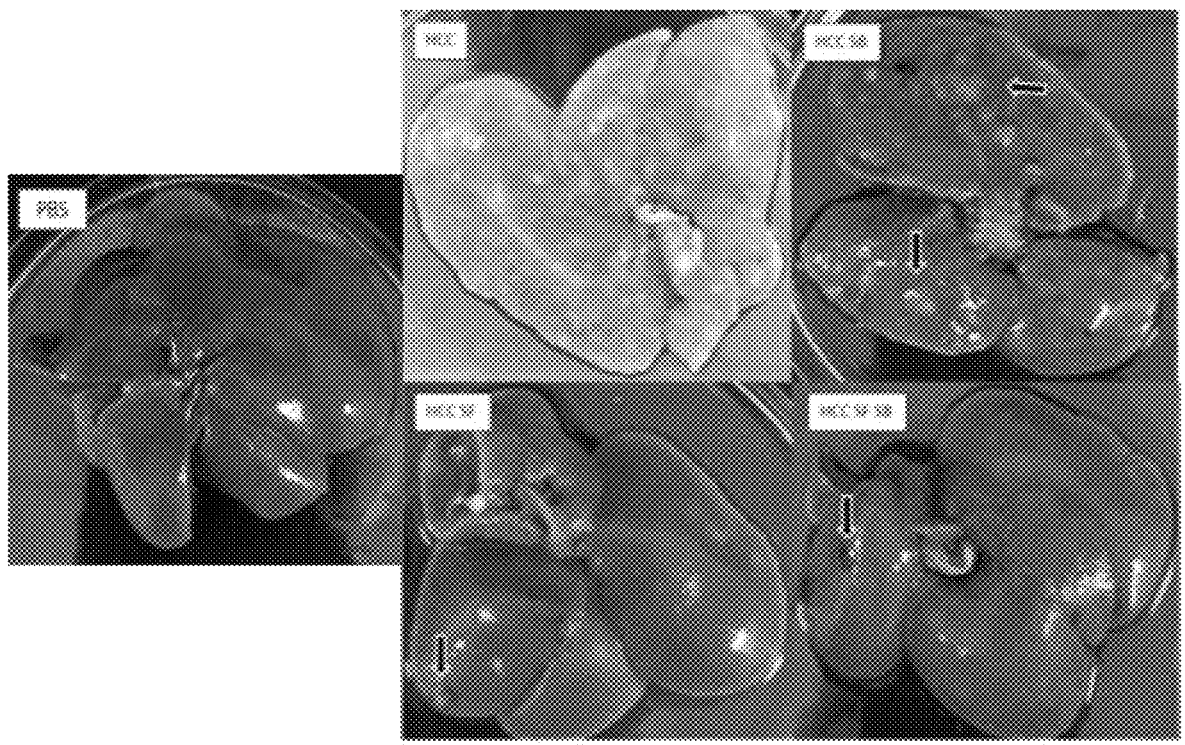
FIG. 2 provides representative images of rat livers demonstrating the anti-tumorigenic properties of safranal. Whole livers were excised from control rats (PBS), DEN-induced hepatic neoplasia in rats untreated (HCC group) or treated with sorafenib (HCC SB), safranal (HCC SF) individually or combined (HCC SF SB).

Anti-tumorigenic and Anti-proliferative Activities of Safranal on DEN Induced Rat Liver Tumors Liver Gross FIG. 2 includes representative images of livers on week 20 to demonstrate the antitumorigenic effect of safranal (n=6). Whole liver excised from control rats (PBS), DEN-induced hepatic neoplasia in rats untreated (HCC group) or treated with sorafenib (HCC SB), safranal (HCC SF) individually or combined (HCC SF SB). Control PBS liver shows normal liver structure and color with no macroscopic lesions. The treatments showed "lesser levels of damaged livers" compared to livers from HCC group. DEN caused lesions and rough liver surface and caused abnormality in liver color in HCC animals. Drug treatments of HCC rats restored to variable degrees the normal liver architecture where lesions were evidently less in drug-treated groups.

Figure 3:
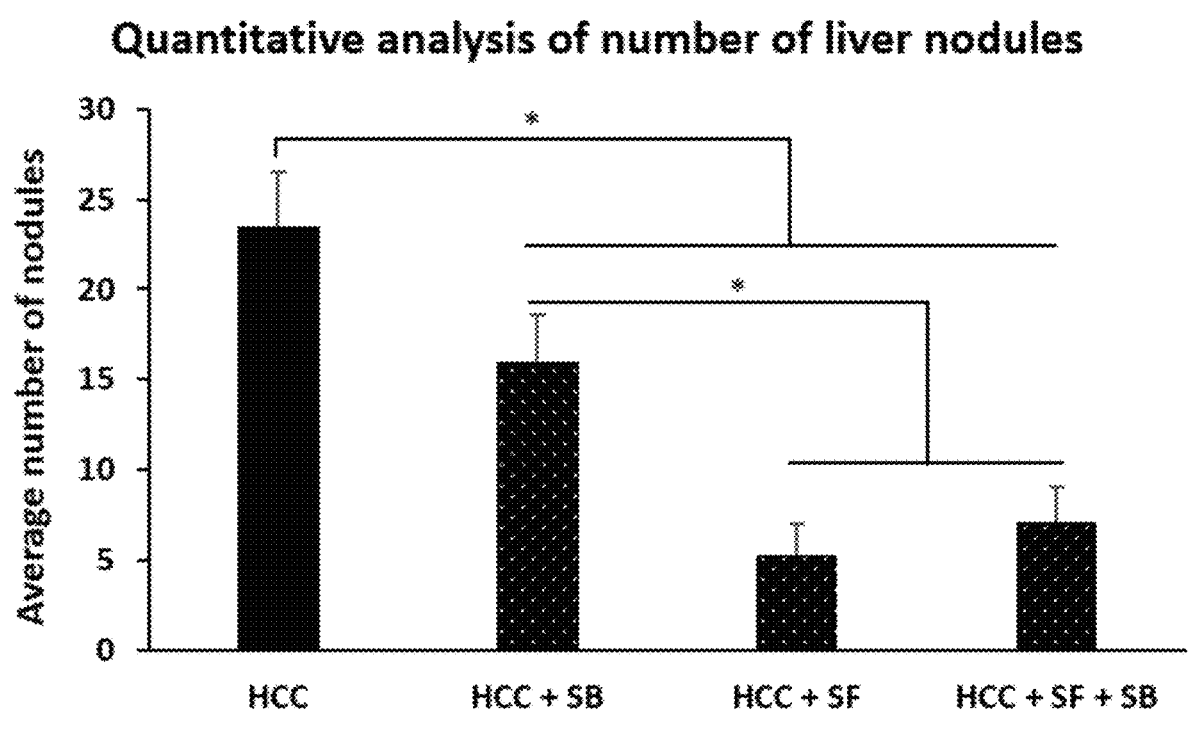
FIG. 3 provides a quantitative analysis of the number of liver nodules from DEN-induced hepatic neoplasia in rats untreated (HCC group) or treated with sorafenib (HCC+SB), safranal (HCC+SF) individually or combined (HCC+SF+SB).

FIG. 3 provides a quantitative analysis of the number of liver nodules from DEN-induced hepatic neoplasia in rats untreated (HCC group) or treated with sorafenib (HCC+SB), safranal (HCC+SF) individually or combined (HCC+SF+SB). Significance was determined by one-way ANOVA followed by Tukey's post hoc analysis (P<0.05). Treatments with safranal (HCC+safranal) and with both safranal and sorafenib (HCC+safranal+sorafenib) reduced lesions comparing to HCC animals, safranal also dramatically decreased lesions comparing to treatment with sorafenib alone (HCC+sorafenib).

Histology

Figure 4:
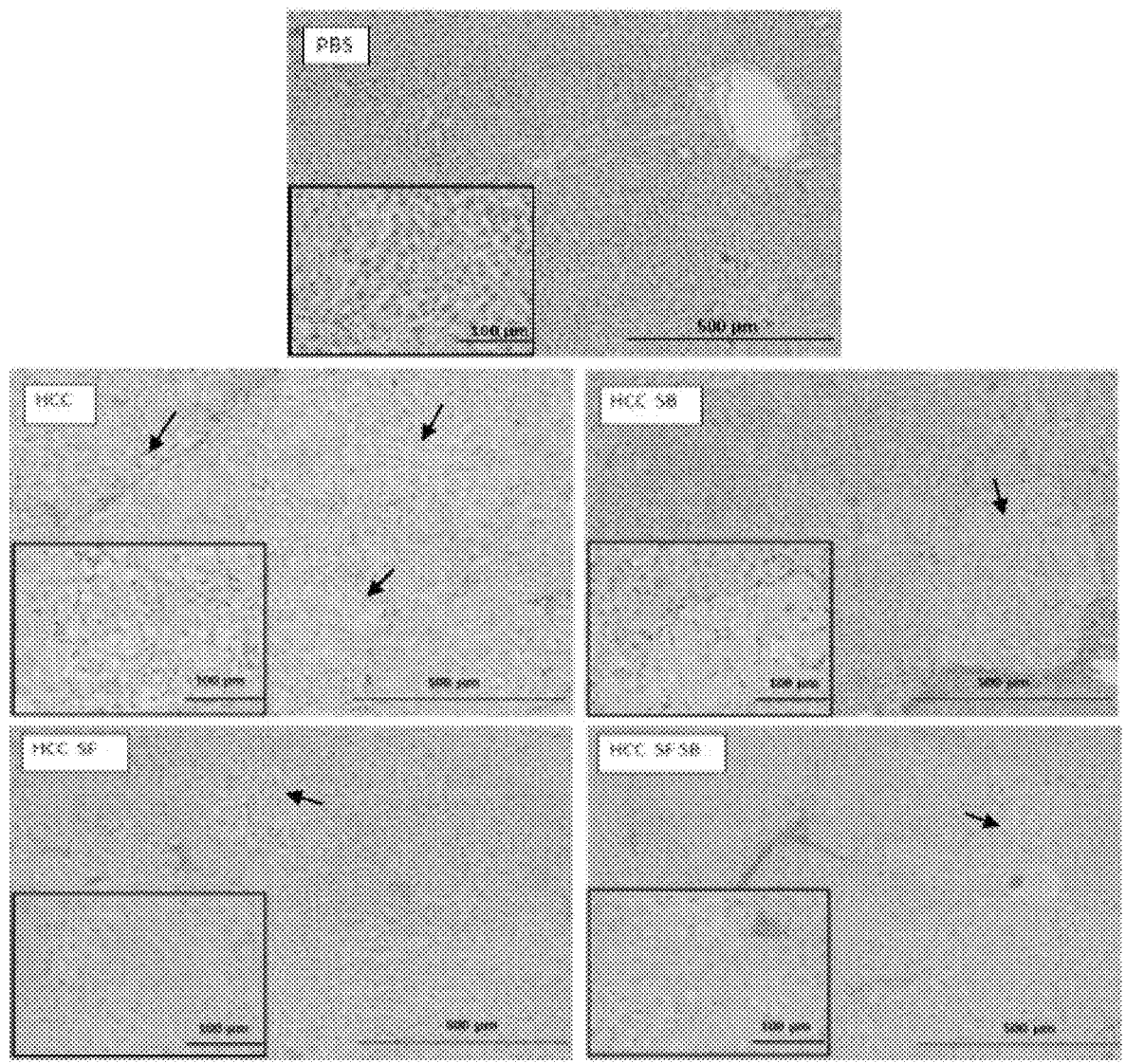
FIG. 4 provides representative images of hematoxylin and eosin-stained sections (arrows point to representative areas of AHF), n=6. The sections were of livers from control rats (PBS), DEN-induced hepatic neoplasia in rats untreated (HCC group) or treated with sorafenib (HCC SB), safranal (HCC SF) individually or combined (HCC SF SB).

FIG. 4 includes representative images of hematoxylin and eosin-stained sections (arrows point to representative areas of AHF), n=6. Sections were taken from: control rats (PBS), DEN induced hepatic neoplasia in rats untreated (HCC group) or treated with sorafenib (HCC SB), safranal (HCC SF) individually or combined (HCC SF SB). The structure of tissues and cells need to be stained in order to be visible. Cellular components are normally stained with a different color for proper distinction and analysis. Hematoxylin stains nucleic acids (nucleus) with blue color. Eosin stains proteins (cytoplasm) with pink color. The stain reveals plentiful structural and functional information (Fischer et al., 2008). Normal structure and histology of liver as seen in the control group where the liver is organized into hexagonally shaped lobules with the central vein at lobular centers. Hepatocytes are arranged in single-cell thick plates that radiate out from the central vein. In the animal model that has been developed in this study, macroscopic nodules were observed in the livers of mainly DEN-induced groups (see FIG. 2). However, microscopic histological examination of livers of rats in DEN-induced group showed clear neoplastic changes such as altered hepatocellular foci (AHF). In the present study, AHF are usually distinguished as delineated areas of hepatocytes with altered staining properties. Treatment with safranal either alone or in combination with sorafenib seem to enhance the restoration of the normal architecture of the liver in DEN-treated groups.

Figure 5:
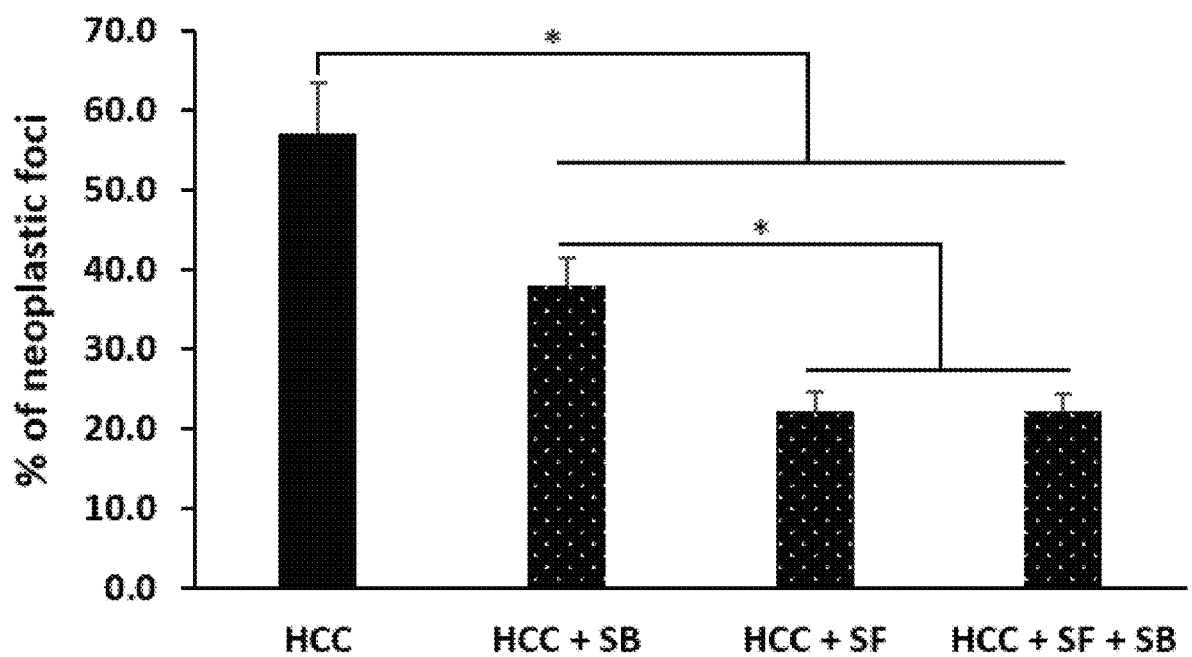
FIG. 5 provides a quantitative analysis of the area of neoplastic foci for histology from DEN-induced hepatic neoplasia in rats that were untreated (HCC group) or treated with sorafenib (HCC+SB), safranal (HCC+SF) individually or combined (HCC+SF+SB).

FIG. 5 provides a quantitative analysis of the area of neoplastic foci for histology from DEN-induced hepatic neoplasia in rats that were untreated (HCC group) or treated with sorafenib (HCC+SB), safranal (HCC+SF) individually or combined (HCC+SF+SB). Significance was determined by one-way ANOVA followed by Tukey's post hoc analysis (P<0.05). The analysis shows that safranal either alone or in combination with sorafenib seems to enhance (P<0.05) the restoration of the normal architecture of the liver in DEN-treated groups.

Reticulin Staining

Figure 6:
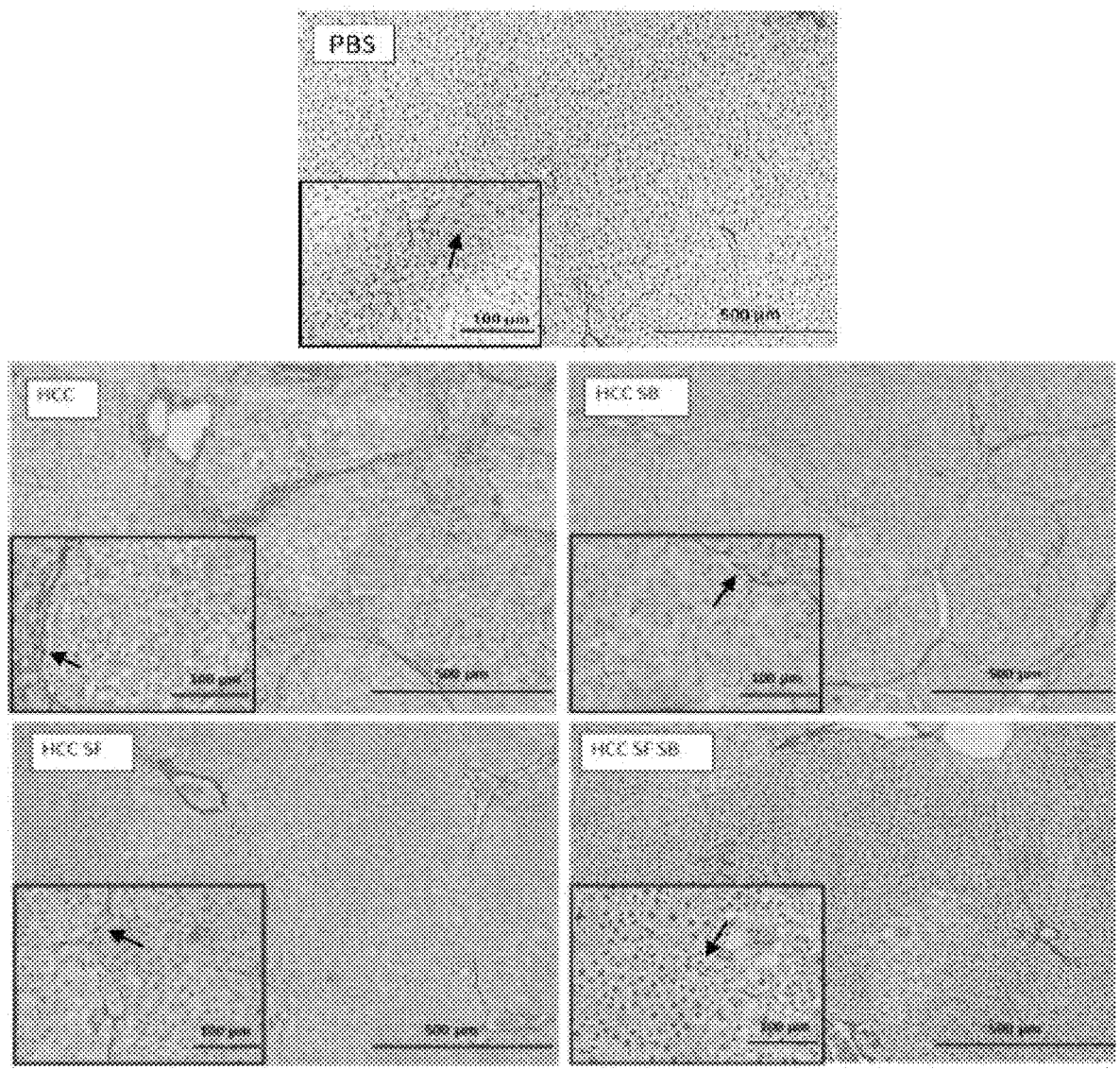
FIG. 6 provides representative images of reticulin-stained sections (arrows point to reticulin fibers). The sections were taken from control rats (PBS), DEN-induced hepatic neoplasia in rats untreated (HCC group) or treated with sorafenib (HCC SB), safranal (HCC SF) individually or combined (HCC SF SB).

FIG. 6 provides representative light microscope images of reticulin-stained sections (arrows point to reticulin fibers). The sections were taken from control rats (PBS), DEN-induced hepatic neoplasia in rats untreated (HCC group) or treated with sorafenib (HCC SB), safranal HCC SF) individually or combined (HCC SF SB). Control PBS liver shows normal liver morphology and defined reticular fibers. Liver sections from HCC animals show that DEN has caused reticular fiber breakage indicating hepatic neoplasia diagnosis. Treatment with safranal (HCC+safranal) and with both safranal and sorafenib (HCC+safranal+sorafenib) reduced reticular fibers' breakage and restored their morphology comparing to HCC group, showing more intact bundles of reticulin fibers, and smaller lesions compared to their counterparts in livers of animals treated with sorafenib alone (HCC+sorafenib).

Anti-Proliferative Effect of Safranal

Figure 7A:
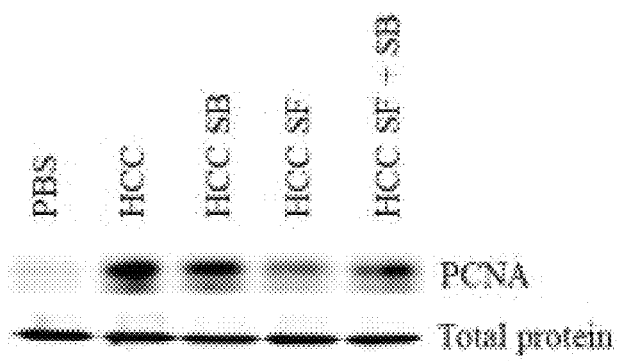
FIGS. 7A and 7B demonstrate that safranal inhibits proliferation of induced hepatic neoplasia.
Figure 7B:
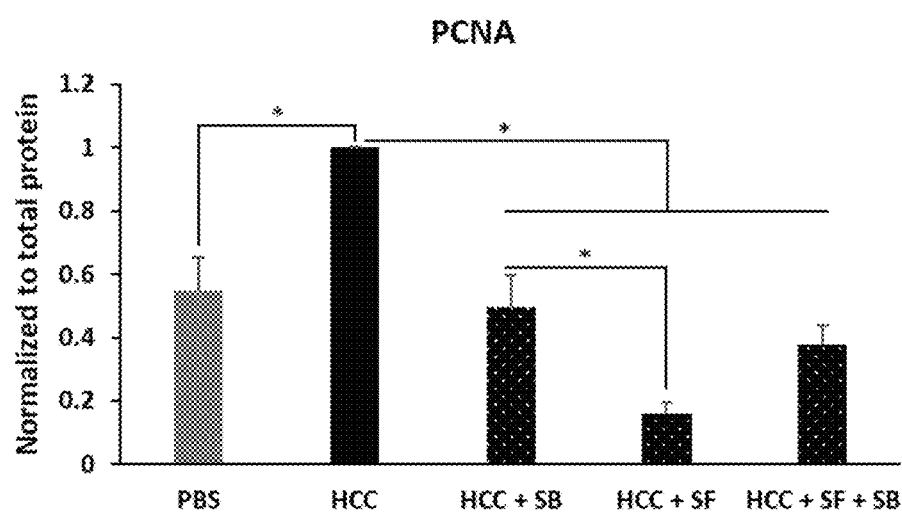

As shown in the western blot results of FIG. 7, safranal inhibits proliferation of induced hepatic neoplasia. FIG. 7A is a western blot analysis of the proliferation-related protein (PCNA) on DEN-induced hepatic neoplasia in rats untreated (HCC group) or treated with sorafenib (HCC SB), safranal (HCC SF) individually or combined (HCC SF+SB). In FIG. 7B, each band intensity was quantified using ImageJ, normalized in relative to the total protein from the liver. Results are expressed as mean±S.D for n=4 animals in each group. Significance was determined by one-way ANOVA followed by Tukey's post hoc analysis (P<0.05). The results showed that PCNA was significantly (P<0.05) increased in DEN induced livers comparing to controls, while treatment with safranal (P<0.05) and with both safranal and sorafenib (P<0.05) significantly downregulated PCNA.

Effect of Safranal on Cell Cycle Progression

Figure 8:
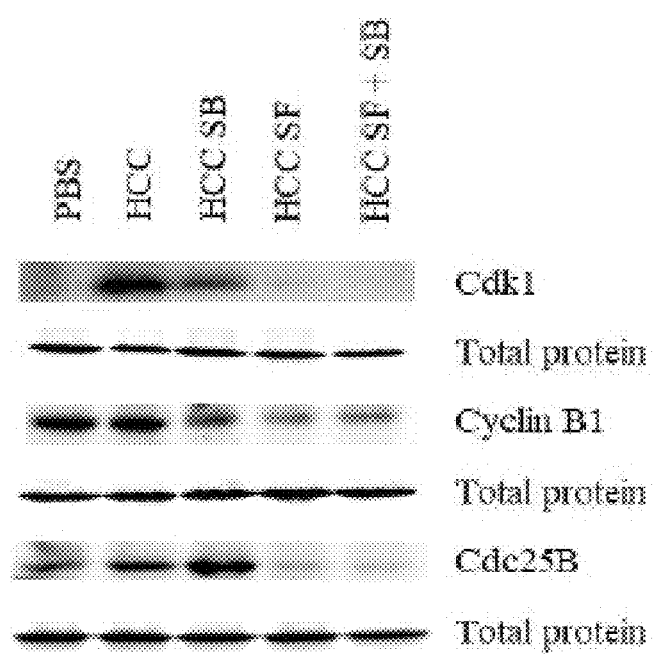
FIG. 8 is a western blot analysis of the cell cycle-related proteins (Cdk1, Cyclin B1, Cdc25B) on DEN-induced hepatic neoplasia in rats untreated (HCC group) or treated with sorafenib (HCC SB), safranal (HCC SF) individually or combined (HCC SF+SB).
Figure 9:
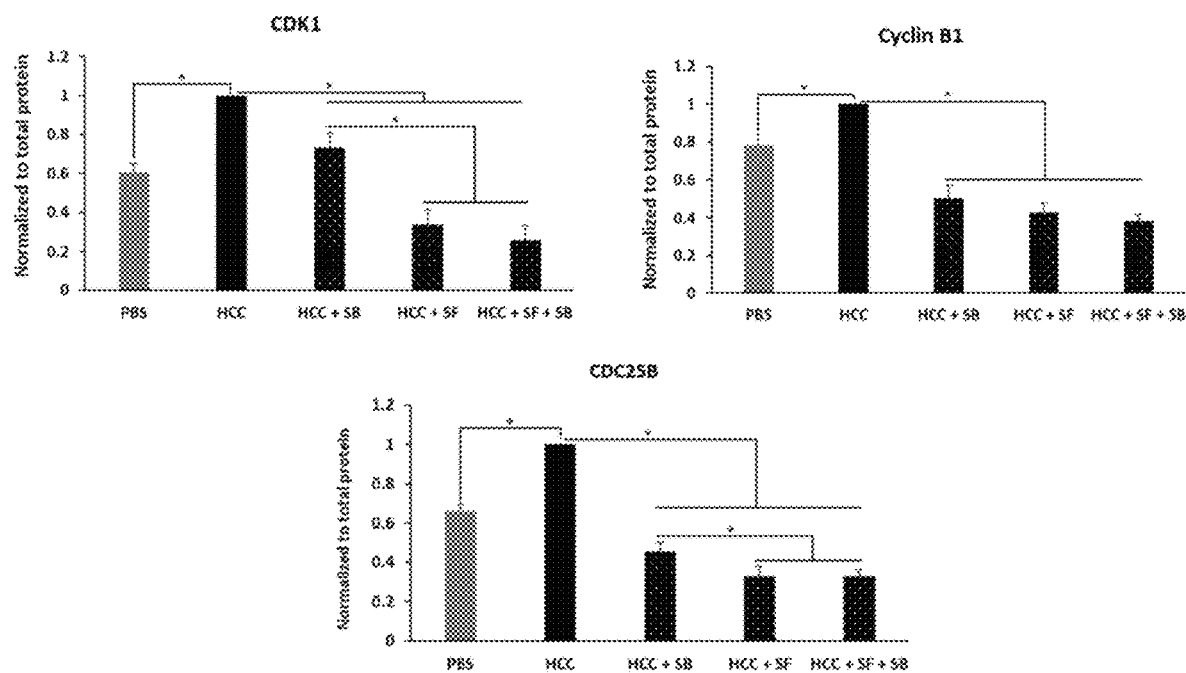
FIG. 9 reports the quantification of proteins of G2/M cell cycle arrest of induced hepatic neoplasia. Each band intensity from FIG. 8 was quantified using ImageJ, normalized in relative to the total protein from the liver. Results are expressed as mean±S.D for (n=4) animals in each group. Significance was determined by one-way ANOVA followed by Tukey's post hoc analysis (P<0.05).

To study the pathway responsible for safranal mediated cell cycle effect in DEN-induced rat liver neoplasia, the expression levels of cell cycle-related proteins were examined. Cdk1, cyclin B1, Cdc25B western blot results (FIG. 8) showed that they are significantly (P<0.05) increased in HCC animals as compared to control animals. Treatment in (HCC+safranal) and (HCC+safranal+sorafenib) groups significantly decreased their levels (P<0.05) comparing to HCC animals. Treatment with safranal (HCC+safranal) and the combination drug (HCC+safranal+sorafenib) showed a greater decrease than treatment with sorafenib alone (HCC+sorafenib) (FIG. 9). Without being bound to any particular theory, it is possible then that safranal may sensitize hepatic cells to sorafenib's effect by further decreasing the expression of cell cycle-related proteins in the co-treated group. These results suggest that safranal causes G2/M cell cycle arrest of drug-treated hepatic cells.

Effect of Safranal on Apoptosis

Figure 10:
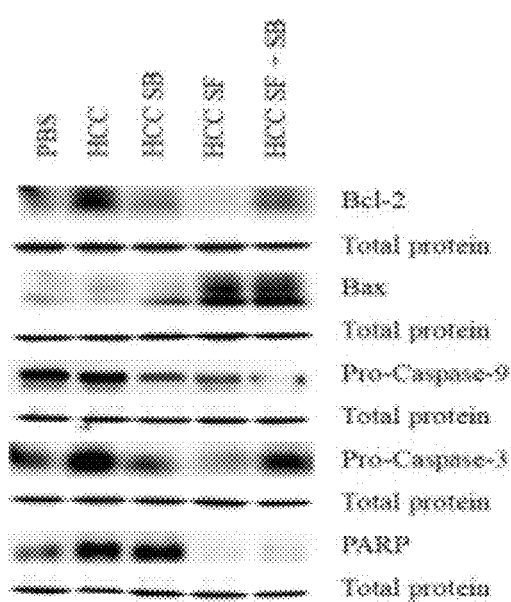
FIG. 10 is a western blot analysis establishing that safranal induces intrinsic apoptosis of induced hepatic neoplasia. The western blot analyzes the intrinsic apoptosis-related proteins (Bcl-2, Bax, Pro-Caspase-9, Pro-Caspase-3, PARP) on DEN-induced hepatic neoplasia in rats untreated (HCC group) or treated with sorafenib (HCC SB), safranal (HCC SF) individually or combined (HCC SF+SB).
Figure 11:
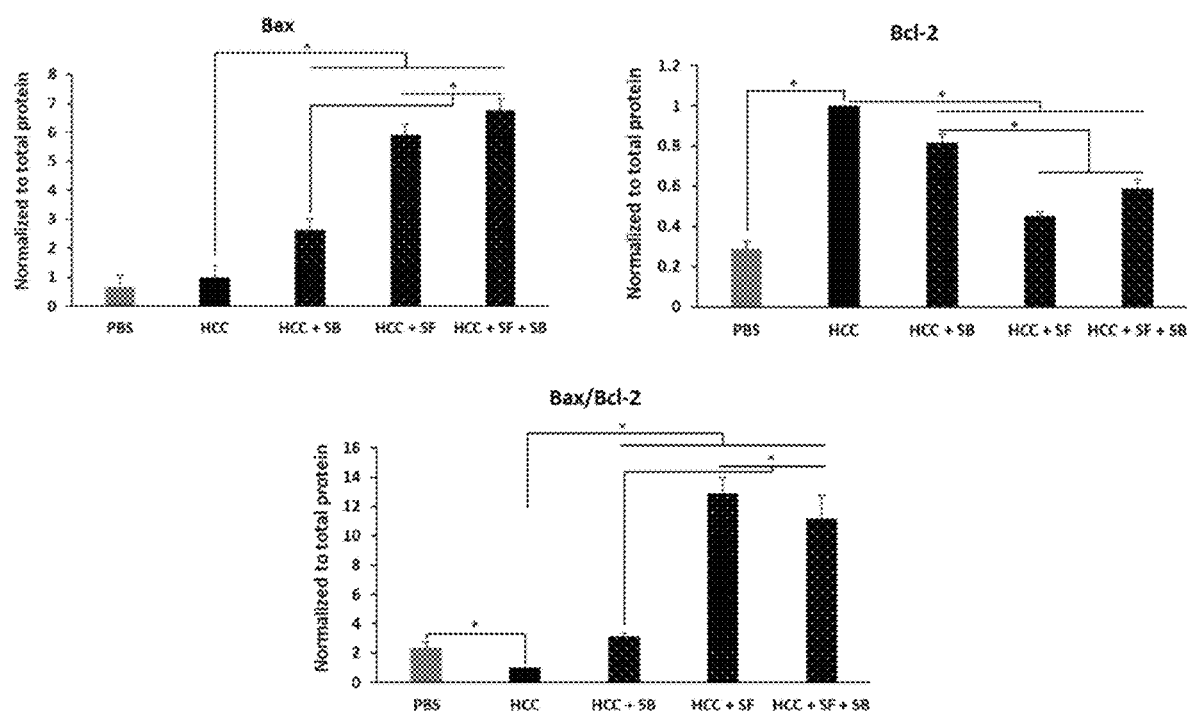
FIG. 11 provides the results of a quantification of Bax, Bcl-2, and the Bax/Bcl ratio from the bands of the western blot of FIG. 10. Each band intensity was quantified using ImageJ, normalized in relative to the total protein from the liver. Results are expressed as mean±S.D for (n=4) animals in each group. Significance was determined by one-way ANOVA followed by Tukey's post hoc analysis (P<0.05).

To study the pathway responsible for safranal mediated apoptosis in DEN-induced rat liver tumor cells, the expression levels of apoptosis-related proteins were examined in the western blot of FIG. 10. The results showed that safranal treatment significantly (P<0.05) increased the expression of the pro-apoptotic protein Bax and significantly (P<0.05) decreased the expression of the anti-apoptotic protein Bcl-2 compared to HCC groups. The Bax/Bcl-2 ratio favored the apoptotic effect of safranal (P<0.05) in DEN-induced rat liver tumors (FIG. 11).

Figure 12:
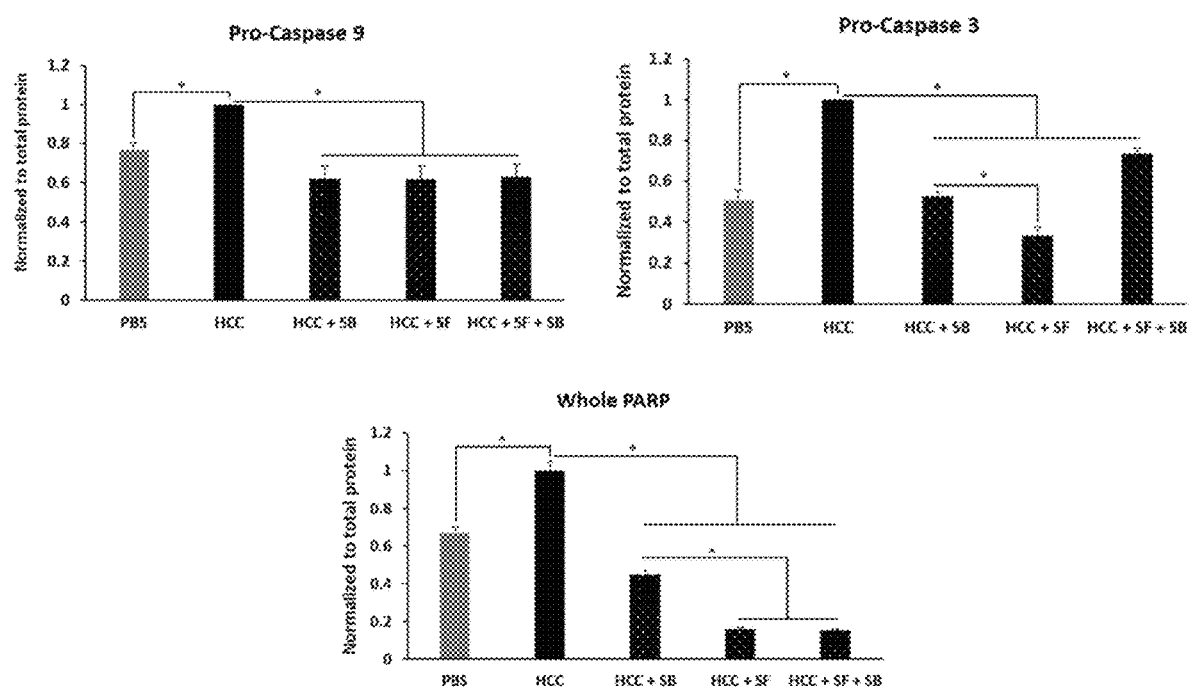
FIG. 12 provides the results of a quantification of Pro-Caspase-9, Pro-Caspase-3, and PARP from the bands of the western blot of FIG. 10. Each band intensity was quantified using ImageJ, normalized in relative to the total protein from the liver. Results are expressed as mean±S.D for (n=4) animals in each group. Significance was determined by one-way ANOVA followed by Tukey's post hoc analysis (P<0.05).

To further investigate the apoptotic effect of safranal, western blot analysis showed that pro-caspase-9, pro-caspase-3, and PARP results confirmed caspase cascade activation and PARP cleavage, where the expression of pro-caspases-9 & 3 and whole PARP were significantly decreased compared to HCC group after treatments with safranal (P<0.05) and with both safranal+sorafenib (P<0.05) (FIG. 12). Interestingly, safranal seemed to help sorafenib-induced PARP cleavage in the animal group treated with both safranal and sorafenib.

Gene Expression Study

Figure 14:
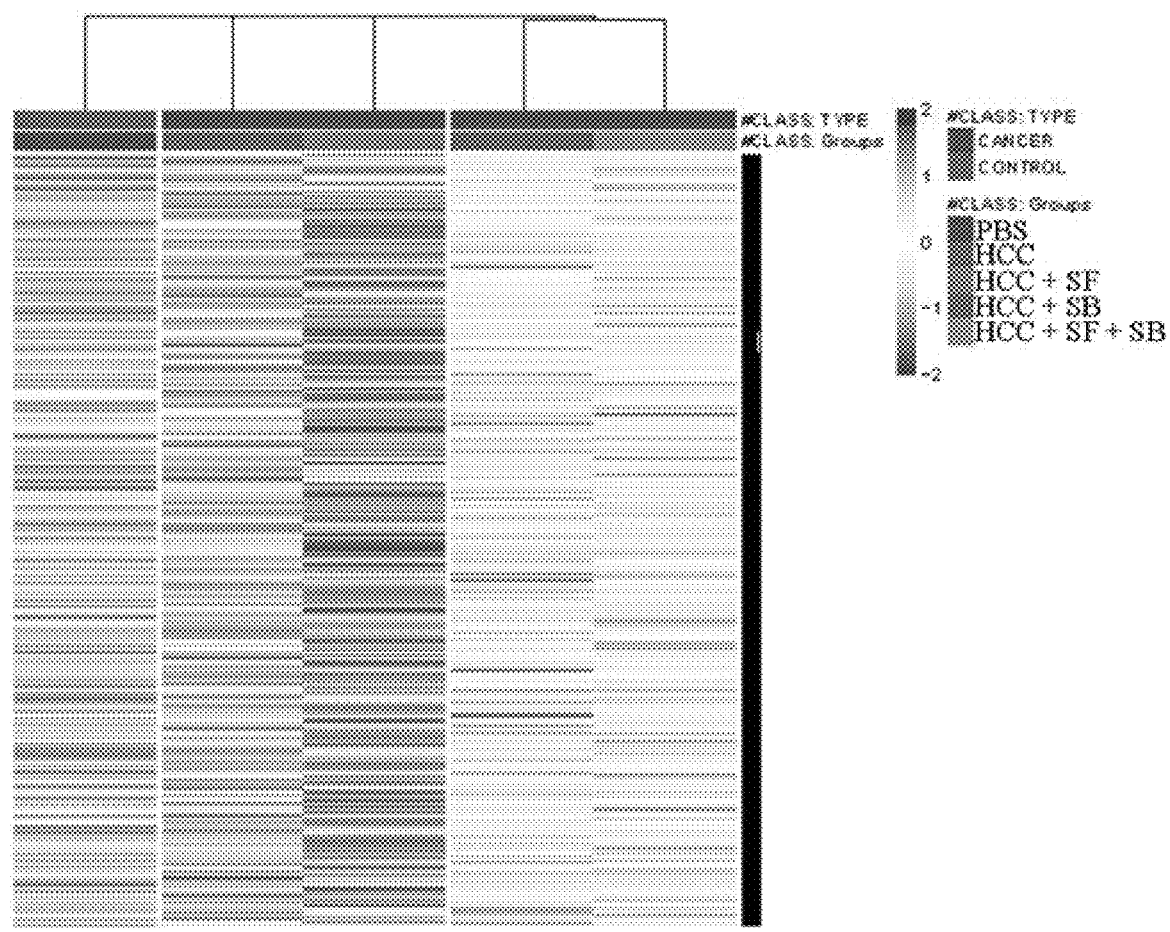
FIG. 14 provides a heatmap of gene expression profiles for all the groups. Hierarchical cluster analysis represents the mean of the triplicate for each group. Raw data were centred and unit variance scaling was applied. Groups were clustered by maximum distance and complete linkage. Expression levels are colored red for high expression and grey for low expression.

Out of whole data set of 32884 sequenced genes, 2400 genes were selected randomly to view an overall expression pattern among the different groups through hierarchical cluster analysis. FIG. 14 provides a heatmap of gene expression profiles for all the groups. Hierarchical cluster analysis represents the mean of the triplicate for each group. Raw data were centered and unit variance scaling was applied. Groups were clustered by maximum distance and complete linkage. Expression levels are colored red for high expression and grey for low expression. This analysis displayed visibly distinguishable patterns across the groups as it detached the experimental groups/cancer induced groups from the control PBS group as expected. Experimental groups (HCC+sorafenib) and (HCC+safranal+sorafenib) clustered closely together leaving HCC group and (HCC+safranal) nearby. Through the aid of color code, it is quite strikingly the difference of gene pattern of (HCC+safranal) to other groups.

Definitions

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein for describing ranges, e.g., of ratios, doses, times, and the like, the terms "about" embraces variations that are within the relevant margin of error, essentially the same (e.g., within an art-accepted confidence interval such as 95% for phenomena that follow a normal or Gaussian distribution), or otherwise does not materially change the effect of the thing being quantified.

As used herein, the term "pro-drug" defined as an inactive form of the drug that is metabolized after administration to a subject to produce the drug having a biological effect.

What is claimed is:

1. A therapeutic combination of drugs for the treatment of a liver cancer, the combination comprising:
   safranal or a pharmaceutically acceptable safranal salt, hydrate, hemiacetal, acetal, thioacetal, silylether, tautomer, or isomer thereof, and
   sorafenib,
   wherein the safranal or pharmaceutically acceptable safranal salt, hydrate, hemiacetal, acetal, thioacetal, silylether, tautomer, or isomer thereof and the sorafenib are present in a mass-to-mass ratio of 50:1 to 1:1.

2. The therapeutic combination of drugs of claim 1, where the safranal and the sorafenib are compounded together in a same unitary pharmaceutical composition including both compounds.

3. The therapeutic combination of drugs of claim 1, where the safranal and the sorafenib are in separate pharmaceutical compositions.

4. The therapeutic combination of drugs of claim 1, wherein the safranal or pharmaceutically acceptable safranal salt, hydrate, hemiacetal, acetal, thioacetal, silylether, tautomer, or isomer thereof and the sorafenib are present in a mass-to-mass ratio of 25:1 to 1:1.

5. The therapeutic combination of drugs of claim 1, wherein the safranal or pharmaceutically acceptable safranal salt, hydrate, hemiacetal, acetal, thioacetal, silylether, tautomer, or isomer thereof is formulated in solid form.

6. The therapeutic combination of drugs of claim 1, wherein the safranal or pharmaceutically acceptable safranal salt, hydrate, hemiacetal, acetal, thioacetal, silylether, tautomer, or isomer thereof is formulated in liquid form.

7. A kit for the treatment of liver cancer, the kit comprising:
   a first pharmaceutically acceptable composition of safranal,
   a second pharmaceutical composition of sorafenib, and
   instructions for the administration of the first composition and second composition for treatment of liver cancer,
   wherein the first pharmaceutically acceptable composition of safranal and the second pharmaceutical composition of sorafenib are present in a mass-to-mass ratio of 50:1 to 1:1 in the kit.

8. The kit of claim 7, where the liver cancer is selected from the group consisting of hepatocellular carcinoma (HCC), fibrolamellar HCC, cholangiocarcinoma, angiosarcoma, a metastatic liver cancer, and combinations thereof.

9. The kit of claim 7, where the liver cancer is hepatocellular carcinoma.

10. A method of treating, suppressing, or reducing the severity of a liver cancer in a subject, the method comprising administering to the subject the therapeutic combination of claim 1.

11. The method of claim 10, where the liver cancer is selected from the group consisting of hepatocellular carcinoma (HCC), fibrolamellar HCC, cholangiocarcinoma, angiosarcoma, a metastatic liver cancer, and combinations thereof.

12. The method of claim 10, where the liver cancer is hepatocellular carcinoma.

13. The method of claim 10, where the mass-to-mass ratio of safranal:sorafenib is based on the amounts of safranal and sorafenib administered to the subject in a single day, a single week, 14 days, 21 days, or 28 days.

14. The method of claim 10, where the amount of the safranal or a pharmaceutically acceptable safranal salt, hydrate, hemiacetal, acetal, thioacetal, silylether, tautomer, or isomer thereof is from about 10 mg/day to about 1000 mg/day per kg body weight of the subject.

15. The method of claim 10, where the amount of the safranal or a pharmaceutically acceptable safranal salt, hydrate, hemiacetal, acetal, thioacetal, silylether, tautomer, or isomer thereof is from about 200 mg/day to about 750 mg/day per kg body weight of the subject.

16. The method of claim 1, where the amount of the safranal or a pharmaceutically acceptable safranal salt, hydrate, hemiacetal, acetal, thioacetal, silylether, tautomer, or isomer thereof is from about 250 mg/day to about 500 mg/day per kg body weight of the subject.

17. The method of claim 10, where the safranal is administered to the subject prior to the sorafenib, concurrently with the sorafenib, or after the sorafenib.

18. The method of claim 10, where the sorafenib is administered to the subject in an amount of about 800, 600, 400, or 200 mg/day.

19. The method of claim 10, where the sorafenib is administered at an effective dose that is at least 50% to at most 90% or more below the dose needed to be effective in the absence of safranal administration.

20. The method of claim 10, where the liver cancer has primary or secondary resistance to sorafenib.

* * * * *

UNITED STATES PATENT AND TRADEMARK OFFICE
CERTIFICATE OF CORRECTION

PATENT NO.       : 10,568,873 B1
APPLICATION NO.  : 16/275878
DATED            : February 25, 2020
INVENTOR(S)      : Amin et al.

Page 1 of 1

It is certified that error appears in the above-identified patent and that said Letters Patent is hereby corrected as shown below:

Column 18, Claim 16, Line 3, "claim 1", should be --claim 10--.

Signed and Sealed this
Twenty-fifth Day of August, 2020

Andrei Iancu
*Director of the United States Patent and Trademark Office*